(12) United States Patent
Haeuw et al.

(10) Patent No.: US 8,178,096 B2
(45) Date of Patent: May 15, 2012

(54) USE OF AN ANTI-CD151 ANTIBODY IN THE TREATMENT OF CANCER

(75) Inventors: Jean-Francois Haeuw, Beaumont (FR); Liliane Goetsch, Ayze (FR)

(73) Assignee: Pierre Fabre Medicament, Boulogne Billancourt (FR)

( * ) Notice: Subject to any disclaimer, the term of this patent is extended or adjusted under 35 U.S.C. 154(b) by 0 days.

(21) Appl. No.: 12/311,682

(22) PCT Filed: Oct. 15, 2007

(86) PCT No.: PCT/FR2007/001688
§ 371 (c)(1),
(2), (4) Date: Apr. 7, 2009

(87) PCT Pub. No.: WO2008/049990
PCT Pub. Date: May 2, 2008

(65) Prior Publication Data
US 2009/0324600 A1 Dec. 31, 2009

(30) Foreign Application Priority Data
Oct. 18, 2006 (FR) .................................. 06 09135

(51) Int. Cl.
*A61K 39/395* (2006.01)
(52) U.S. Cl. .................................. 424/139.1; 424/174.1
(58) Field of Classification Search ............... 424/139.1, 424/174.1
See application file for complete search history.

(56) References Cited

U.S. PATENT DOCUMENTS
2010/0150902 A1* 6/2010 Haeuw ........................ 424/130.1

FOREIGN PATENT DOCUMENTS
JP 2003321494 11/2003
WO 9966027 12/1999

OTHER PUBLICATIONS

Voskoglou-Nomikos (Clin. Can. Res. 9:4227-4239 (2003)).*
Dennis (Nature 442:739-741 (2006)).*
Cespdes et al. (Clin. Transl. Oncol. 8(5):318-329 (2006)).*
Talmadge et al. (Am. J. Pathol 170(3):793-804 (2007)).*
Fujimori et al. (J. Nuc. Med. 31:1191-1198 (1990)).*
Beckman et al. (Can. 109:170-179 (2007)).*
Thurber et al. (Adv. Drug Deliv. Rev. 60:1421-1434 (2008)).*
Rudnick et al. (Can. Biotherp. & Radiopharm. 24: 155-162 (2009)).*
Brooks et al. (J. Cell. Biol. 122:1351-1359 (1993)).*
J.E. Testa, et al., "Eukaryotic expression cloning with an antimetastatic monoclonal antibody identifies a tetraspanin (PETA-3/CD 151) as an effector of human tumor cell migration and metastasis" American Association for Cancer Research, vol. 59, No. 15, p. 3812-3820, Aug. 1, 1999.
V. Serru, et al., "Selective tetraspan-integrin complexes (CD81/alpha4beta1, CD151/alpha3beta1, CD151/alpha6beta1) under conditions disrupting tetraspan interactions" The Biochemical Journal, vol. 340, p. 103-111, May 15, 1999.
S.M. Geary, et al., "Differential tissue expression of epitopes of the tetraspain CD151 recognised by monoclonal antibodies" Tissue Antigens, vol. 58, No. 3, p. 141-153, Sep. 2001.
Chometon, et al., "Dissociation of the complex betweenCD151 and laminin-binding intergrins permits migrationof epithelial cells" Experimental Cell Research, vol. 312, No. 7, p. 983-995, Apr. 15, 2006.
Andries Zijlstra, et al. "The inhibition of tumor cell intravasation and subsequent metastasis via regulation of in vivo tumor cell motility by the tetraspanin CD151" Cancer Cell, vol. 13, No. 3, p. 221-234, Mar. 2008.
International Search report for PCT/FR2007/001688 of Jul. 10, 2008.
French Preliminary Search Report for FR0609135 of Jun. 1, 2007.
Adams, et al. Nature Biotechnology 23:1147-1157, 2005.
Ang, et al. Cancer Epidemiol Biomarkers Prev 13:1717-1721, 2004.
Gesierich, et al. Clinical Cancer Research 11:2840-2852, 2005.
Hashida, et al. British Journal of Cancer 89:158-167, 2003.
Takuhara, et al. Clinical Cancer Research 7:4109-4114, 2001.
Hauew, et al. Biochemical Society Transactions, 39:553-558, 2011.
Kohno, et al. Int. J. Cancer 97:336-343, 2002.
Notice of Opposition of European Patent EP2079482. dated Nov. 22, 2011.
Yasunori English Language Translation of JP2003321494.

* cited by examiner

*Primary Examiner* — Lynn Bristol
(74) *Attorney, Agent, or Firm* — Hueschen and Sage

(57) ABSTRACT

The present invention relates to the use of at least one antibody, or a functional fragment thereof, which is capable of binding to the CD151 protein and thereby inhibiting tumor growth, in the preparation of a medicament intended for the treatment of cancer.
The invention is also directed to a composition for the treatment of cancer, comprising, as active ingredient, at least one anti-CD151 antibody, or a functional fragment thereof, which is capable of binding to the CD151 protein and/or of inhibiting the development of primary tumors and/or of inhibiting its metastasis-promoting activity, which antibodies may consist of the antibodies TS151 and/or TS151r.

11 Claims, 6 Drawing Sheets

CD 151

Nucleotide sequence

```
atggtgagt tcacgagaa gaagacaaca tgtggcacg tttgcctcaa gtacctgctg
tttacctaca attgctgctt ctggtgggct ggctggctg tcatggcagt gggcatctgg
acgctggccc tcaagagtga ctacatcagc ctgctggcct caggcaccta cctggccaca
                       SC1
gcctacatcc tggtggtggc gggcactgtc gtcatggtga ctgggtctt gggctgctgc
gccaccttca ggagcgtcg gaacctgctg cgcctgtact tcatcctgct cctcatcatc
tttctgctgg agatcatcgc tggtatcctc gctacggct actaccagca gctgaacacg
gagctcaagg agaacctgaa ggacaccatg accagcgct accaccaggc gggccatgag
gctgtgacca gcgctgtgga ccagctgcag caggagttcc actgctgtgg cagcaacaac
                                SC2
tcacaggact ggcgagacag tgagtggatc cgctcacagg aggccggtgg ccgtgtggtc
ccagacagct gctgcaagac ggtggtgget ctttgtgggc agcgagacca tgcctccaac
atctacaagg tggagggcgg ctgcatcacc aagttggaga ccttcatcca ggagcacctg
aggtcattg gggctgtggg gatcggcatt gctgtgtgc aggtctttgg catgatcttc
acgtgctgcc tgtacaggag tctcaagctg gagcactac
```

Protein sequence (1 letter code)

```
MGEFNEKKTT CGTVCLKYLL FTYNCCFWLA GLAVMAVGIW TLALKSDYIS
                                            SC1
LLASGTYLAT AYILVVAGTV VMVTGVLGCC AFFSRRNLL RLYFILLIII
FLLEIIAGIL AYYQQLNT ELKENLKDTM TSRYHQQGHE AVTSAVDQLQ
QEFHCCGSNN SQDWRDSEWI RSQEAGGRVV PDSCCKTVVA LCGQRDHASN
                               SC2
IYKVEGGCIT KLETFIQEHL RVIGAVGIGI ACVQVFGMIF TCCLYRSLKL
EHY
```

Figure 1

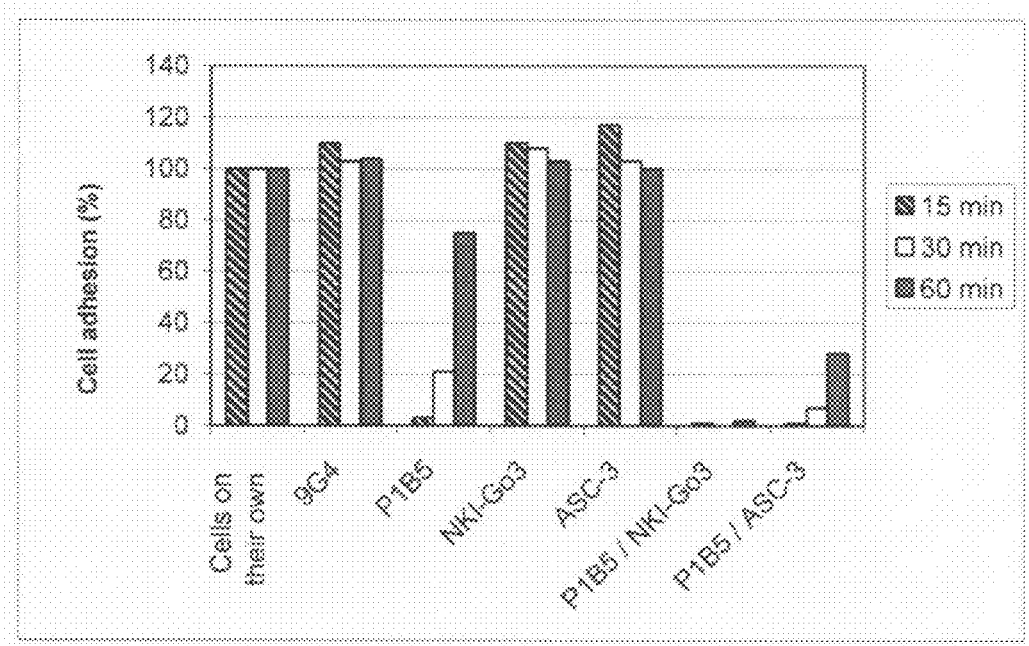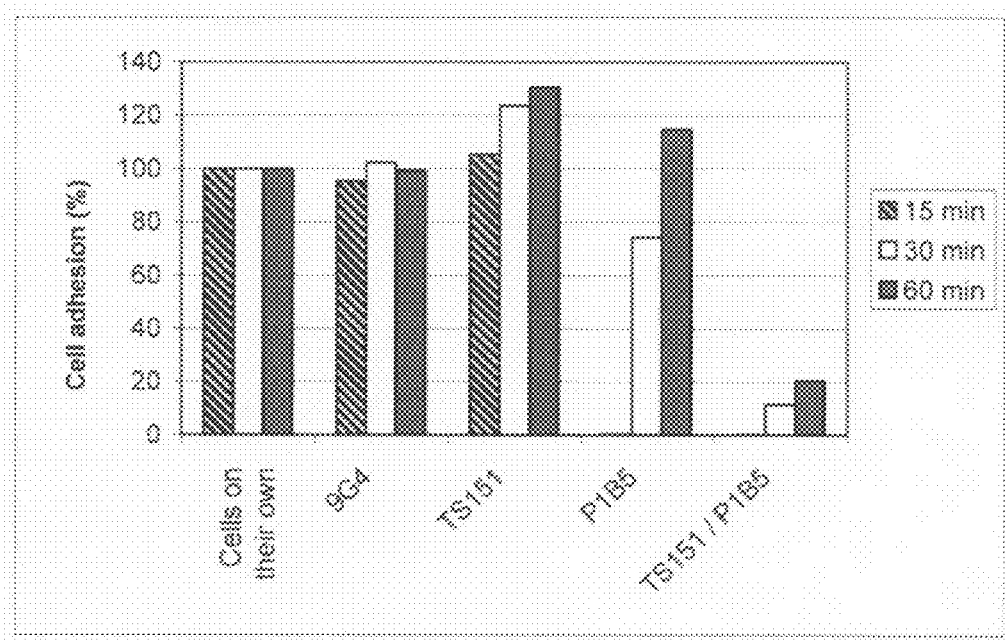
Figure 9

SEQUENCE LISTING

<160> NUMBER OF SEQ ID NOS: 38

<210> SEQ ID NO 1
<211> LENGTH: 759
<212> TYPE: DNA
<213> ORGANISM: Homo sapiens

<400> SEQUENCE: 1

```
atgggtgagt tcaacgagaa gaagacaaca tgtggcaccg tttgcctcaa gtacctgctg      60
tttacctaca attgctgctt ctggctggct ggcctggctg tcatggcagt gggcatctgg     120
acgctggccc tcaagagtga ctacatcagc ctgctggcct caggcaccta cctggccaca     180
gcctacatcc tggtggtggc gggcactgtc gtcatggtga ctggggtctt gggctgctgc     240
gccaccttca aggagcgtcg gaacctgctg cgcctgtact tcatcctgct cctcatcatc     300
tttctgctgg agatcatcgc tggtatcctc gcctacgcct actaccagca gctgaacacg     360
gagctcaagg agaacctgaa ggacaccatg accaagcgct accaccagcc gggccatgag     420
gctgtgacca gcgctgtgga ccagctgcag caggagttcc actgctgtgg cagcaacaac     480
tcacaggact ggcgagacag tgagtggatc cgctcacagg aggccggtgg ccgtgtggtc     540
ccagacagct gctgcaagac ggtggtggct ctttgtgggc agcgagacca tgcctccaac     600
atctacaagg tggagggcgg ctgcatcacc aagttggaga ccttcatcca ggagcacctg     660
agggtcattg gggctgtggg gatcggcatt gcctgtgtgc aggtctttgg catgatcttc     720
acgtgctgcc tgtacaggag tctcaagctg gagcactac                            759
```

<210> SEQ ID NO 2
<211> LENGTH: 253
<212> TYPE: PRT
<213> ORGANISM: homo sapiens

<400> SEQUENCE: 2

```
Met Gly Glu Phe Asn Glu Lys Lys Thr Thr Cys Gly Thr Val Cys Leu
1               5                   10                  15

Lys Tyr Leu Leu Phe Thr Tyr Asn Cys Cys Phe Trp Leu Ala Gly Leu
            20                  25                  30
```

Ala Val Met Ala Val Gly Ile Trp Thr Leu Ala Leu Lys Ser Asp Tyr
            35                  40                  45

Ile Ser Leu Leu Ala Ser Gly Thr Tyr Leu Ala Thr Ala Tyr Ile Leu
        50                  55                  60

Val Val Ala Gly Thr Val Val Met Val Thr Gly Val Leu Gly Cys Cys
65                  70                  75                  80

Ala Thr Phe Lys Glu Arg Arg Asn Leu Leu Arg Leu Tyr Phe Ile Leu
                85                  90                  95

Leu Leu Ile Ile Phe Leu Leu Glu Ile Ala Gly Ile Leu Ala Tyr
            100                 105                 110

Ala Tyr Tyr Gln Gln Leu Asn Thr Glu Leu Lys Glu Asn Leu Lys Asp
            115                 120                 125

Thr Met Thr Lys Arg Tyr His Gln Pro Gly His Glu Ala Val Thr Ser
        130                 135                 140

Ala Val Asp Gln Leu Gln Gln Glu Phe His Cys Cys Gly Ser Asn Asn
145                 150                 155                 160

Ser Gln Asp Trp Arg Asp Ser Glu Trp Ile Arg Ser Gln Glu Ala Gly
                165                 170                 175

Gly Arg Val Val Pro Asp Ser Cys Cys Lys Thr Val Ala Leu Cys
            180                 185                 190

Gly Gln Arg Asp His Ala Ser Asn Ile Tyr Lys Val Glu Gly Gly Cys
            195                 200                 205

Ile Thr Lys Leu Glu Thr Phe Ile Gln Glu His Leu Arg Val Ile Gly
        210                 215                 220

Ala Val Gly Ile Gly Ile Ala Cys Val Gln Val Phe Gly Met Ile Phe
225                 230                 235                 240

Thr Cys Cys Leu Tyr Arg Ser Leu Lys Leu Glu His Tyr
            245                 250

<210> SEQ ID NO 3
<211> LENGTH: 327
<212> TYPE: DNA
<213> ORGANISM: homo sapiens

<400> SEQUENCE: 3
gcctactacc agcagctgaa cacggagctc aaggagaacc tgaaggacac catgaccaag      60
cgctaccacc agccgggcca tgaggctgtg accagcgctg tggaccagct gcagcaggag     120
ttccactgct gtggcagcaa caactcacag gactggcgag acagtgagtg gatccgctca     180
caggaggccg gtggccgtgt ggtcccagac agctgctgca agacggtggt ggctcttTgt     240
gggcagcgag accatgcctc caacatctac aaggtggagg gcggctgcat caccaagttg     300
gagaccttca tccaggagca cctgagg                                         327

<210> SEQ ID NO 4
<211> LENGTH: 109
<212> TYPE: PRT
<213> ORGANISM: homo sapiens

<400> SEQUENCE: 4

Ala Tyr Tyr Gln Gln Leu Asn Thr Glu Leu Lys Glu Asn Leu Lys Asp
1               5                   10                  15

Thr Met Thr Lys Arg Tyr His Gln Pro Gly His Glu Ala Val Thr Ser
            20                  25                  30

Ala Val Asp Gln Leu Gln Gln Glu Phe His Cys Cys Gly Ser Asn Asn
        35                  40                  45

```
Ser Gln Asp Trp Arg Asp Ser Glu Trp Ile Arg Ser Gln Glu Ala Gly
        50                  55                  60

Gly Arg Val Val Pro Asp Ser Cys Cys Lys Thr Val Val Ala Leu Cys
 65                  70                  75                  80

Gly Gln Arg Asp His Ala Ser Asn Ile Tyr Lys Val Glu Gly Cys
                 85                  90                  95

Ile Thr Lys Leu Glu Thr Phe Ile Gln Glu His Leu Arg
            100                 105
```

<210> SEQ ID NO 5
<211> LENGTH: 54
<212> TYPE: DNA
<213> ORGANISM: homo sapiens

<400> SEQUENCE: 5
tggacgctgg ccctcaagag tgactacatc agcctgctgg cctcaggcac ctac        54

<210> SEQ ID NO 6
<211> LENGTH: 18
<212> TYPE: PRT
<213> ORGANISM: homo sapiens

<400> SEQUENCE: 6

```
Trp Thr Leu Ala Leu Lys Ser Asp Tyr Ile Ser Leu Leu Ala Ser Gly
 1               5                  10                  15

Thr Tyr
```

<210> SEQ ID NO 7
<211> LENGTH: 8
<212> TYPE: PRT
<213> ORGANISM: mus musculus

<400> SEQUENCE: 7

```
Gly Tyr Thr Phe Thr Asp Tyr Ser
 1               5
```

<210> SEQ ID NO 8
<211> LENGTH: 8
<212> TYPE: PRT
<213> ORGANISM: mus musculus

<400> SEQUENCE: 8

```
Ile Asn Thr Glu Thr Gly Glu Pro
 1               5
```

<210> SEQ ID NO 9
<211> LENGTH: 13
<212> TYPE: PRT
<213> ORGANISM: mus musculus

<400> SEQUENCE: 9

```
Ala Arg Arg Glu Tyr Gly Asn Tyr Tyr Gly Met Glu Tyr
 1               5                  10
```

<210> SEQ ID NO 10
<211> LENGTH: 120
<212> TYPE: PRT
<213> ORGANISM: mus musculus -continued

<400> SEQUENCE: 10

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Lys Gly Leu Lys Trp Met
        35                  40                  45

Gly Trp Ile Asn Thr Glu Thr Gly Glu Pro Thr Tyr Thr Asp Asp Phe
    50                  55                  60

Lys Gly Arg Phe Ala Phe Ser Leu Glu Thr Ser Ala Asn Thr Ala Tyr
65                  70                  75                  80

Leu Arg Ile Asn Asn Leu Lys Asn Glu Asp Thr Ala Thr Tyr Phe Cys
                85                  90                  95

Ala Arg Arg Glu Tyr Gly Asn Tyr Tyr Gly Met Glu Tyr Trp Gly Gln
            100                 105                 110

Gly Thr Ser Val Thr Val Ser Ser
        115                 120

<210> SEQ ID NO 11
<211> LENGTH: 10
<212> TYPE: PRT
<213> ORGANISM: mus musculus

<400> SEQUENCE: 11

Gln Ser Val Ser Thr Ser Thr Phe Ser Tyr
1               5                   10

<210> SEQ ID NO 12
<211> LENGTH: 3
<212> TYPE: PRT
<213> ORGANISM: mus musculus

<400> SEQUENCE: 12

Ser Ala Ser
1

<210> SEQ ID NO 13
<211> LENGTH: 9
<212> TYPE: PRT
<213> ORGANISM: mus musculus

<400> SEQUENCE: 13

Gln His Ser Trp Glu Ile Pro Leu Thr
1               5

<210> SEQ ID NO 14
<211> LENGTH: 111
<212> TYPE: PRT
<213> ORGANISM: mus musculus

<400> SEQUENCE: 14

Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Thr Phe Ser Tyr Ile His Trp Tyr Gln Gln Lys Pro Gly Gln Pro Pro
        35                  40                  45

Lys Leu Leu Ile Lys Ser Ala Ser Asn Leu Glu Ser Gly Val Pro Ala
    50                  55                  60

```
Arg Phe Ser Gly Ser Gly Ser Gly Thr Asp Phe Thr Leu Thr Ile His
 65                  70                  75                  80

Pro Val Glu Glu Glu Asp Thr Ala Thr Tyr Phe Cys Gln His Ser Trp
                 85                  90                  95

Glu Ile Pro Leu Thr Phe Gly Ala Gly Thr Lys Leu Glu Leu Lys
            100                 105                 110
```

<210> SEQ ID NO 15
<211> LENGTH: 8
<212> TYPE: PRT
<213> ORGANISM: mus musculus

<400> SEQUENCE: 15

```
Gly Tyr Thr Phe Thr Ser Ser Trp
 1               5
```

<210> SEQ ID NO 16
<211> LENGTH: 8
<212> TYPE: PRT
<213> ORGANISM: mus musculus

<400> SEQUENCE: 16

```
Ile His Pro Asn Ser Gly Asn Thr
 1               5
```

<210> SEQ ID NO 17
<211> LENGTH: 16
<212> TYPE: PRT
<213> ORGANISM: mus musculus

<400> SEQUENCE: 17

```
Ala Arg Gly Asp Asp Ala Tyr Tyr Ser Gly Leu Tyr Ala Met Asp Tyr
 1               5                   10                  15
```

<210> SEQ ID NO 18
<211> LENGTH: 123
<212> TYPE: PRT
<213> ORGANISM: mus musculus

<400> SEQUENCE: 18

```
Gln Val Gln Leu Gln Gln Pro Gly Ser Val Val Arg Pro Gly Ala
 1               5                   10                  15

Ser Val Lys Leu Ser Cys Lys Ala Ser Gly Tyr Thr Phe Thr Ser Ser
                 20                  25                  30

Trp Met His Trp Ala Lys Gln Arg Pro Gly Gln Gly Leu Glu Trp Ile
            35                  40                  45

Gly Gln Ile His Pro Asn Ser Gly Asn Thr Asn Tyr Asn Glu Lys Phe
        50                  55                  60

Lys Val Lys Ala Thr Leu Thr Ile Asp Thr Ser Ser Ser Thr Ala Tyr
 65                  70                  75                  80

Val Asp Leu Asn Ser Leu Thr Ser Gly Asp Ser Ala Val Tyr Tyr Cys
                 85                  90                  95

Ala Arg Gly Asp Asp Ala Tyr Tyr Ser Gly Leu Tyr Ala Met Asp Tyr
            100                 105                 110

Trp Gly Gln Gly Thr Ser Val Thr Val Ser Ser
            115                 120
```

<210> SEQ ID NO 19
<211> LENGTH: 10
<212> TYPE: PRT
<213> ORGANISM: mus musculus

<400> SEQUENCE: 19

Gln Ser Val Ser Thr Ser Arg Tyr Ser Tyr
1               5                   10

<210> SEQ ID NO 20
<211> LENGTH: 3
<212> TYPE: PRT
<213> ORGANISM: mus musculus

<400> SEQUENCE: 20

Tyr Ala Ser
1

<210> SEQ ID NO 21
<211> LENGTH: 9
<212> TYPE: PRT
<213> ORGANISM: mus musculus

<400> SEQUENCE: 21

Gln His Ser Trp Glu Ile Pro Tyr Thr
1               5

<210> SEQ ID NO 22
<211> LENGTH: 111
<212> TYPE: PRT
<213> ORGANISM: mus musculus

<400> SEQUENCE: 22

Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Arg Tyr Ser Tyr Met His Trp Tyr Gln Gln Ile Gln Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr His Cys Gln His Ser Trp
                85                  90                  95

Glu Ile Pro Tyr Thr Phe Gly Gly Gly Thr Thr Leu Glu Ile Lys
            100                 105                 110

<210> SEQ ID NO 23
<211> LENGTH: 24
<212> TYPE: DNA
<213> ORGANISM: mus musculus

<400> SEQUENCE: 23
ggttatacct tcacagacta ttca                                          24

<210> SEQ ID NO 24
<211> LENGTH: 24
<212> TYPE: DNA
<213> ORGANISM: mus musculus

<400> SEQUENCE: 24
ataaacactg agactggtga gcca                                          24

```
<210> SEQ ID NO 25
<211> LENGTH: 39
<212> TYPE: DNA
<213> ORGANISM: mus musculus

<400> SEQUENCE: 25
gctagaaggg agtatggtaa ctactatggt atggagtac                       39

<210> SEQ ID NO 26
<211> LENGTH: 360
<212> TYPE: DNA
<213> ORGANISM: mus musculus

<400> SEQUENCE: 26
cagatccagt tggtgcagtc tggacctgag ctgaagaagc ctggagagac agtcaagatc    60
tcctgcaagg cttctggtta taccttcaca gactattcaa tgcactgggt gaagcaggct   120
ccaggaaagg gtttaaagtg gatgggctgg ataaacactg agactggtga gccaacatat   180
acagatgact tcaagggacg gtttgccttc tctttggaaa cctctgccaa cactgcctat   240
ttgcggatca caacctcaa aaatgaggac acggctacat atttctgtgc tagaagggag   300
tatggtaact actatggtat ggagtactgg ggtcaaggaa cctcagtcac cgtctcgtca   360

<210> SEQ ID NO 27
<211> LENGTH: 30
<212> TYPE: DNA
<213> ORGANISM: mus musculus

<400> SEQUENCE: 27
caaagtgtca gtacatctac ctttagttat                                 30

<210> SEQ ID NO 28
<211> LENGTH: 9
<212> TYPE: DNA
<213> ORGANISM: mus musculus

<400> SEQUENCE: 28 tctgcatcc                                                         9

<210> SEQ ID NO 29
<211> LENGTH: 27
<212> TYPE: DNA
<213> ORGANISM: mus musculus

<400> SEQUENCE: 29
cagcacagtt gggagattcc gctcacg                                    27

<210> SEQ ID NO 30
<211> LENGTH: 333
<212> TYPE: DNA
<213> ORGANISM: mus musculus

<400> SEQUENCE: 30
gacattgtgc tgacacagtc tcctgcttcc ttagctgtat ctctggggca gagggccacc    60
atctcatgca gggccagcca aagtgtcagt acatctacct ttagttatat acactggtac   120
caacagaaac caggacagcc acccaaactc ctcatcaagt ctgcatccaa cctagaatct   180
ggggtccctg ccaggttcag tggcagtggg tctgggacag acttcaccct caccatccat   240
cctgtggagg aggaggatac tgcaacatat ttctgtcagc acagttggga gattccgctc   300
acgttcggtg ctgggaccaa gctggagctg aaa                              333
```

<210> SEQ ID NO 31
<211> LENGTH: 24
<212> TYPE: DNA
<213> ORGANISM: mus musculus

<400> SEQUENCE: 31
ggctacacct tcaccagctc ctgg                                          24

<210> SEQ ID NO 32
<211> LENGTH: 24
<212> TYPE: DNA
<213> ORGANISM: mus musculus

<400> SEQUENCE: 32
attcatccta atagtggtaa tact                                          24

<210> SEQ ID NO 33
<211> LENGTH: 48
<212> TYPE: DNA
<213> ORGANISM: mus musculus

<400> SEQUENCE: 33
gcaagagggg atgatgctta ctacagcggg ctctatgcta tggactac                48

<210> SEQ ID NO 34
<211> LENGTH: 369
<212> TYPE: DNA
<213> ORGANISM: mus musculus

<400> SEQUENCE: 34
caggtccaac tgcagcagcc tgggtctgtg gtggtgaggc ctggagcttc agtgaaactg    60
tcctgcaagg cttctggcta caccttcacc agctcctgga tgcactgggc gaagcagagg   120
cctggacaag gccttgagtg gattggacag attcatccta atagtggtaa tactaattac   180
aatgagaagt tcaaggtcaa ggccacactg actatagaca catcctccag cacagcctac   240
gtggatctca acagcctgac atctggggac tctgcggtct attactgtgc aagagggat    300 gatgcttact acagcgggct ctatgctatg gactactggg gtcagggaac ctcagtcacc   360
gtctcctca                                                          369

<210> SEQ ID NO 35
<211> LENGTH: 30
<212> TYPE: DNA
<213> ORGANISM: mus musculus

<400> SEQUENCE: 35
caaagtgtca gtacatctag gtatagttat                                    30

<210> SEQ ID NO 36
<211> LENGTH: 9
<212> TYPE: DNA
<213> ORGANISM: mus musculus

<400> SEQUENCE: 36 tatgcatcc                                                            9

<210> SEQ ID NO 37
<211> LENGTH: 27
<212> TYPE: DNA
<213> ORGANISM: mus musculus

```
<400> SEQUENCE: 37
caacacagtt gggagattcc gtacacg                                          27

<210> SEQ ID NO 38
<211> LENGTH: 333
<212> TYPE: DNA
<213> ORGANISM: mus musculus

<400> SEQUENCE: 38
gacattgtgc tgacacagtc tcctgcttcc ttagctgtat ctctggggca gagggccacc      60
atctcatgca gggccagcca aagtgtcagt acatctaggt atagttatat gcactggtac     120
caacagatac aaggacagcc acccaaactc ctcatcaagt atgcatccaa cctagaatct     180
ggggtccctg ccaggttcag tggcagtggg tctgggacag acttcaccct caacatccat     240
cctgtggagg aggaggatac tgcaacatat cactgtcaac acagttggga gattccgtac     300
acgttcggag gggggaccac gctggaaata aaa                                  333
```

USE OF AN ANTI-CD151 ANTIBODY IN THE TREATMENT OF CANCER

The present invention relates to a new use of anti-CD151 antibodies capable of inhibiting tumour growth, said antibodies being especially monoclonal of murine origin, chimaeric and humanised. According to a particular aspect, the invention relates to the use of those antibodies, or of functional fragments thereof, as medicaments for the prophylactic and/or therapeutic treatment of cancers. Finally, the invention includes products and/or compositions comprising such antibodies in association, for example, with anti-cancer agents and/or antibodies or conjugated with toxins, and use thereof in the prevention and/or treatment of certain cancers.

CD151, also referred to as PETA-3 or SFA-1, is a membrane protein belonging to the tetraspanin family (Boucheix and Rubinstein, 2001, Cell Mol. Life Sci. 58, 1189-1205; Hemler, 2001, J. Cell Biol. 155, 1103-1107). In humans, CD151 has 253 amino acids and includes 4 membrane fragments and 2 extracellular domains EC1 (18 amino acids, sequence [40-57]) and EC2 (109 amino acids, sequence [113-221]) which are also referred to as extracellular loops. It is to be noted, however, that, in the nucleotide sequence, two variants of CD151 have been identified hitherto, namely one having nucleotides A and C at positions 395 and 409, respectively, (SEQ ID No. 1) [Fitter et al., 1995, Blood 86(4), 1348-1355] and the other having, at the same positions, nucleotides G and T instead of nucleotides A and C [Hasegawa et al., 1996, J. Virol. 70(5), 3258-3263]. As a result, a mutation can be observed in the peptide sequence, namely a mutation of the residues K (Lys) and P (Pro) at positions 132 and 137, respectively, to the residues R (Arg) and S (Ser) [Fitter et al., 1995, Blood 86(4), 1348-1355/Hasegawa et al., 1996, J. Virol. 70(5), 3258-3263].

CD151 is overexpressed in numerous cancers such as, for example, cancers of the lung [Tokuhara et al., 2001, Clin. Cancer Res. 7, 4109-4114], colon [Hashida et al., 2003, Br. J. Cancer 89, 158-167], prostate [Ang et al., 2004, Cancer Epidemiol. Biomarkers Prev. 13, 1717-1721] or pancreas [Gesierich et al., 2005, Clin. Cancer Res. 11, 2840-2852].

The use of knock-out mice which do not express CD151 and of anti-CD151 antibodies and siRNA in order to block, in vitro, the functionality and expression of CD151 in various types of cell has allowed it to be shown that CD151 is involved in a number of phenomena related to cancer, such as cell adhesion (Nishiuchi et al., 2005, Proc. Natl. Acad. Sci. USA 102, 1939-1944; Winterwood et al., 2006, Mol. Biol. Cell 17, 2707-2721), cell motility (Kohno et al., 2002, Int. J. Cancer 97, 336-343), cell migration (Yauch et al., 1998, Mol. Biol. Cell 9, 2751-2765; Testa et al., 1999, Cancer Res. 59, 3812-3820; Penas et al., 2000, J. Invest. Dermatol. 114, 1126-1135; Klosek et al., 2005, Biochem. Biophys. Res. Commun. 336, 408-416), cell invasion (Kohno et al., 2002, Int. J. Cancer 97, 336-343; Shiomi et al., 2005, Lab. Invest. 85, 1489-1506; Hong et al., 2006, J. Biol. Chem. 281, 24279-24292) and angiogenesis (Yanez-Mo et al., 1998, J. Cell Biol. 141, 791-804; Sincock et al., 1999, J. Cell Sci. 112, 833-844; Takeda et al., 2006, Blood).

One of the noteworthy properties of the tetraspanins is their ability to form associations amongst themselves and also with a large number of other surface molecules so as to form structured macromolecular complexes. Within those complexes, each tetraspanin is associated specifically with one or more surface molecules, thereby forming primary complexes composed of a tetraspanin and a partner molecule. The tetraspanins are capable of organising particular microdomains of the plasma membrane from which microdomains they may recruit their partner molecules, which may be functionally coupled. The set of interactions involving the tetraspanins has been referred to as the "network of tetraspanins" or "Tetraspanin Web".

CD151 interacts on the surface of cells with various membrane proteins. In particular, there have been identified highly stable complexes, resistant to the action of certain detergents, with laminin receptor integrins, more particularly with the integrins $\alpha 3\beta 4$ or $\alpha 6\beta 4$, whose preferred ligand is laminin 5 (Yauch et al., 1998, Mol. Biol. Cell 9, 2751-2765; Lammerding et al., 2003, Proc. Natl. Acad. Sci. USA 100, 7616-7621). This association involves the extracellular domains of CD151 and the integrins. The sequence QRD [194-196] of CD151, located in the EC2 loop, is very important in that association because mutation of this site causes loss of interaction with certain integrins (Kazarov et al., 2002, J. Cell Biol. 158, 1299-1309). Functional ternary complexes of CD151/integrin $\alpha 6\beta 4$/c-Met (HGF receptor) have moreover been identified in tumour cells (Klosek et al., 2005, Biochem. Biophys. Res. Commun. 336, 408-416). Inhibition of the expression of CD151 as a result of treating cells with an interference RNA results in inhibition of the cell growth and migration caused by HGF.

The interactions, within a particular cell, between CD151 and other tetraspanins, necessary for formation of the network of tetraspanins, are thought to depend on the membrane and cytoplasmic regions of CD151 because it has been shown that deletion of the EC2 loop does not disrupt the association of CD151 with other tetraspanins (Berditchevski, 2001, J. Cell Sci. 114, 4143-4151).

CD151 is capable of regulating the phenomena of cell adhesion, migration and invasion by modulation of various signalling pathways such as, for example, the phosphoinositide pathway via an association with PI4-kinase (Yauch et al., 1998, Mol. Biol. Cell 9, 2751-2765), the c-Jun signalling pathway via the phosphorylation de FAK, Src, p38-MAPK and JNK (Hong et al., 2006), the phosphorylation of integrins by PKC (Zhang et al., 2001, J. Biol. Chem. 276, 25005-25013) and the activation of GTPases of the Rho family (Shigeta et al., 2003, J. Cell Biol. 163, 165-176).

Homophilic-type interactions between cells are also responsible for an increase in cell motility and in expression of the metalloproteinase MMP-9 (Hong et al., 2006). Those intercellular CD151-CD151 interactions bring about the activation of c-Jun via the phosphorylation of FAK, Src, p38-MAPK and JNK.

Despite the interest in the CD151 protein, only one therapeutically aimed antibody has been generated to date, namely the monoclonal antibody 50-6.

The monoclonal antibody 50-6 (IgG 1 isotype) directed to CD151 was generated in the mouse by subtractive immunisations with human epidermoid carcinoma HEp-3 cells (Testa et al., 1999, Cancer Res. 59, 3812-3820).

The antibody 50-6 is capable of inhibiting, in vitro, migration of human cervical carcinoma HeLa cells, transfected so as to overexpress CD151, and of HEp-3 cells and angiogenesis in a model of chorio-allantoic membrane neovascularisation caused by bFGF (basic fibroblast growth factor). In vivo it inhibits the metastases brought about by inoculation of HEp-3 cells in 2 chicken embryo models (Testa et al., 1999, Cancer Res. 59, 3812-3820). In these models, the inhibitory activity of the antibody 50-6 is determined by measurement of the activity of the protein huPA (human urokinase-type plasminogen activator) in lung extracts. According to the authors, this assay reflects the presence of human cells in the lungs. After assaying, the reduction in metastases (dissemination of HEp-3 cells into the chicken embryo lungs) that is brought about by the antibody 50-6 is estimated, by comparison with a control antibody, to be 74% in a so-called "spontaneous metastasis" model, in which inoculation of the cells is followed by injection of the antibody, and 57% in a so-called "experimental metastasis" model, in which the cells and the antibody are inoculated together. According to the authors, the anti-tumour properties of the antibody 50-6 that are observed in vivo do not seem to be related to a cytostatic or cytotoxic effect because the antibody showed no effect on the in vitro proliferation of HEp-3 cells.

The hybridoma producing the antibody 50-6 is available at the ATCC under the reference CRL-2696 (hybridoma initially deposited under the reference 50-6 [PTA-227]).

According to a general aspect, the present invention is directed to use of at least one antibody, or a functional fragment thereof, which is capable of binding to the CD151 protein and thereby inhibiting tumour growth, in the preparation of a medicament intended for the treatment of cancer.

Several experimental studies have shown the major role of the tetraspanins in the formation of metastases by acting either as suppressors or as promoters of metastases. Accordingly, the transfection of tetraspanins such as CD9, CD63 or CD82 reduces the metastatic potential of cancer lines. In contrast, expression of the tetraspanins CD151 and Co-029 seems to produce the opposite effect. These 2 tetraspanins are therefore thought to be promoters of metastasis. These results are consistent with various clinical studies which have shown that, in a number of cancers (breast, lung, oesophagus, stomach, liver, pancreas, colon, prostate, melanoma . . . ), CD9 and CD82 are less expressed in primary tumours when there is metastasis and that a reduction in their expression is predictive of a lower survival rate. In lung cancer, the combined reduction in the expression of CD9 and CD82 has been correlated with greater metastatic potential than when expression of just one of those two antigens is reduced.

Several retrospective studies have shown that overexpression of CD151 is associated with aggressiveness of certain cancers, such as lung, colon and prostate cancers, and that it might be considered to be a factor for poor prognosis (Tokuhara et al., 2001, Clin. Cancer Res. 7, 4109-4114; Hashida et al., 2003, Br. J. Cancer 89, 158-167; Ang et al., 2004, Cancer Epidemiol. Biomarkers Prev. 13, 1717-1721). In these cases, mean survival is in fact reduced in those patients having tumours which express CD151, compared to those having tumours which do not express CD151.

The overexpression of CD151 in various human tumour lines (HeLa, RPMI4788, A172, HT1080), brought about by transfection of the corresponding gene, causes an increase in the motility of, the migration of and invasion by the transfected cells (Testa et al., 1999, Cancer Res. 59, 3812-3820; Kohno et al., 2002, Int. J. Cancer 97, 336-343). These phenomena are inhibited in the presence of anti-CD151 antibodies.

According to another aspect, the functional fragments of antibodies according to the invention consist, for example, of Fv, scFv (sc standing for single chain), Fab, F(ab')$_2$, Fab' or scFv-Fc fragments or diabodies, or any fragment whose half-life may have been extended by chemical modification, e.g. addition of poly(alkylene)glycol such as poly(ethylene)glycol ("PEGylation") (the PEGylated fragments being referred to as Fv-PEG, scFv-PEG, Fab-PEG, F(ab')$_2$-PEG or Fab'-PEG) ("PEG" from the designation Poly(Ethylene)Glycol), or by incorporation in a liposome, microspheres or PLGA, said fragments being capable of generally exerting activity, even partial, of the antibody from which it is derived.

Preferably, said functional fragments will be composed of or will comprise a partial sequence of the variable heavy or light chain of the antibody from which they are derived, said partial sequence being sufficient to retain the same binding specificity as the antibody from which it is derived and an adequate affinity, preferably equal to at least 1/100th, more preferably at least 1/10th, of that of the antibody from which it is derived.

Such a functional fragment will comprise at least 5 consecutive amino acids, preferably 10, 15, 25, 50 or 100 consecutive amino acids, from the sequence of the antibody from which it is derived.

Preferably, these functional fragments will be fragments of Fv, scFv, Fab, F(ab')$_2$, F(ab'), scFv-Fc type, or diabodies, which generally have the same fixing specificity as the antibody from which they are obtained. According to the present invention, fragments of antibodies of the invention can be obtained starting from antibodies as described hereinbefore by methods such as digestion using enzymes such as pepsin or papain and/or by cleavage of the disulfide bridges by means of chemical reduction. The antibody fragments included in the present invention can also be obtained by genetic recombination techniques that are likewise well-known to the person skilled in the art or by peptide synthesis by means of, for example, automatic peptide synthesisers such as those supplied by the company Applied.

According to an aspect of the invention, the antibody used consists of a murine monoclonal antibody.

Antibodies according to the present invention also include chimaeric or humanised antibodies.

A chimaeric antibody is understood as referring to an antibody which contains a natural variable (light chain and heavy chain) region derived from an antibody from a given species in association with the constant light chain and heavy chain regions of an antibody from a heterologous species to said given species.

Chimaeric-type antibodies, or their fragments, used in accordance with the invention can be prepared using genetic recombination techniques. For example, the chimaeric antibody may be produced by cloning a recombinant DNA comprising a promoter and a sequence coding for the variable region of a non-human, especially murine, monoclonal antibody according to the invention and a sequence coding for the constant region of a human antibody. A chimaeric antibody of the invention encoded by such a recombinant gene may be, for example, a mouse-human chimaera, the specificity of that antibody being determined by the variable region derived from the murine DNA and its isotype determined by the constant region derived from the human DNA. For methods of preparing chimaeric antibodies, reference may be made, for example, to the document Verhoeyn et al. (BioEssays, 8:74, 1988).

A humanised antibody is understood as referring to an antibody which contains CDR regions derived from an antibody of non-human origin, the other parts of the antibody molecule being derived from one (or more) human antibody/antibodies. In addition, some of the residues of the segments of the skeleton (referred to as FR) can be modified in order to preserve the binding affinity (Jones et al., Nature, 321:522-525, 1986; Verhoeyen et al., Science, 239:1534-1536, 1988; Riechmann et al., Nature, 332:323-327, 1988).

The humanised antibodies or functional fragments thereof can be prepared by techniques known to the person skilled in the art (such as, for example, those described in the documents Singer et al., J. Immun. 150:2844-2857, 1992; Mountain et al., Biotechnol. Genet. Eng. Rev. 10:1-142, 1992; or Bebbington et al., Bio/Technology, 10:169-175, 1992). Such humanised antibodies are preferred for their use in in vivo prophylactic and/or therapeutic treatment methods. Other humanisation techniques are also known to the person skilled in the art, such as, for example, the technique of "CDR Grafting", described by PDL, which is the subject-matter of patents EP 0 451 261, EP0 682 040, EP 0 939 127, EP 0 566 647 or also U.S. Pat. No. 5,530,101, U.S. Pat. No. 6,180,370, U.S. Pat. No. 5,585,089 and U.S. Pat. No. 5,693,761. There may also be mentioned the U.S. Pat. No. 5,639,641 or also U.S. Pat. Nos. 6,054,297, 5,886,152 and 5,877,293.

Surprisingly, and contrary to any expectation on the part of the person skilled in the art, the present invention describes for the first time the use of an anti-CD151 antibody as described hereinbefore, or one of its functional fragments, which is capable of inhibiting the proliferation of tumour cells and the development of the primary tumour, independently of its ability to inhibit angiogenesis and/or the formation of metastases.

The antibodies described in the Application accordingly have the ability to inhibit the development of tumours at a very early stage.

This anti-tumour activity of the antibodies to which the present invention relates constitutes a new and unexpected property for an antibody directed to CD151, because no hitherto described anti-CD151 antibody has this type of activity. The antibodies to which the present invention relates accordingly have a different, and additional, property compared to the previously described antibodies, especially compared to the 50-6 antibody because the anti-tumour properties of that antibody are not due to an effect on the proliferation of tumour cells.

This result also constitutes the first demonstration of a link between CD151 and the development of the primary tumour, or indeed the in vivo proliferation of tumour cells. Only the pro-metastatic and pro-angiogenic activities of CD151 have in fact been described hitherto.

The disordered proliferation of the cells of an organ or tissue constitutes one of the first stages in cancer. Tumour cells are cells which are no longer subject to the normal cell growth constraints within the organ or tissue concerned. Tumour growth is exponential; and the tumour cells multiply in excessive manner under the effect of growth and angiogenic factors.

According to a main aspect, the invention relates to use of at least one anti-CD151 antibody, or a functional fragment thereof, which is capable of inhibiting the development of the primary tumour and the proliferation of the tumour cells.

More particularly, the present invention relates to the use of at least one antibody, or a functional fragment thereof, which is capable of binding to the CD151 protein, in the preparation of a medicament intended for the treatment of primary tumours.

In addition, the Applicant is putting forward, without wishing to be bound by any such theory, that the use of anti-CD151 antibodies in the context of cancer treatment may be of value not only due to the fact of angiogenesis inhibition but also due to the fact of inhibition of the metastasis-promoting activity of CD151.

The present invention accordingly describes the use of an antibody as described hereinbefore, or a functional fragment thereof, which is capable of inhibiting the metastasis-promoting activity of said CD151 protein within tumour cells.

More particularly, the Applicant thinks that this inhibition takes the form of inhibition of the various stages in the metastatic process, especially cell adhesion, cell migration and/or cell invasion.

The classic steps of said promoting activity, and more particularly of tumour dissemination and the metastatic process, are as follows:

1/ invasion of the underlying tissue by the cells of the primary tumour, requiring degradation by proteolytic enzymes (such as metalloproteinases) of the basal membrane and the extracellular matrix composed of structural proteins such as laminin, collagen or fibronectin, 2/ migration of the tumour cells through the tissues and into the blood stream, 3/ adhesion to the vessel wall and coming to a halt in an organ, 4/ exit from the vessel (new invasion step) and adaptation to the new environment (proliferation and angiogenesis).

Cell migration is essential during development of the embryo. Although cell migration is less substantial in the adult, certain types of cell such as lymphocytes, macrophages and fibroblasts, will continue to move around during the immune response, inflammation and wound healing in the adult in order to maintain homeostasis. However, at the pathological level, migration of tumour cells contributes substantially to the progression of tumours to the metastatic stage. A certain number of chemotactic factors are responsible for that migration, which factors are derived either from the tumour cells or from the host. Amongst those factors there are mentioned growth factors (especially those which stimulate angiogenesis), collagen degradation peptides, adhesion proteins such as laminin and fibronectin.

According to a particular aspect, the invention relates to use of at least one anti-CD151 antibody, or a functional fragment thereof, which is capable of inhibiting the cell migration of tumour cells.

Invasion is the principal sign of the malignancy of a tumour, with the latter breaking away from its original site and moving into neighbouring and distant tissues. The invasive character is a reflection of loss of the customary properties of a cell: normally, the cells of most tissues adhere to one another by structures referred to as desmosomes, by means of adhesive molecules; in an epithelium, they also adhere to the basal membrane which limits it in terms of depth. Tumour cells lose those normal properties and acquire new ones. The links between them are loosened and the cells free themselves from one another. They acquire a mobility which allows them to detach themselves from the primary site and to infiltrate (invade) neighbouring tissues, sometimes following connective tissue fibres. For epithelia normally bounded by a basal membrane and for carcinomas derived therefrom, this membrane is the first obstacle to be crossed. It is degraded and dissolved by enzymes (proteases, cathepsin) secreted by the tumour cells. This destruction of the basal membrane is sometimes accentuated by enzymes normally secreted by white blood cells and diverted from their customary activities. All those biological and molecular modifications of cell behaviour are a condition of invasion.

According to another aspect, the invention relates to use of at least one anti-CD151 antibody, or a functional fragment thereof, which is capable of inhibiting the cell invasion by tumour cells.

The cells of the body adhere to one another and to the extracellular matrix which surrounds them. Cell adhesion is a ubiquitous mechanism involved in most physiological cell phenomena, such as the survival, proliferation or differentiation of cells, but also in various pathological situations such as, for example, cancer and the phenomenon of metastasis. Various cell surface proteins are involved in cell adhesion, such as the cadherins or the integrins.

Preferably, the use according to the invention is based mainly on the inhibition of cell adhesion.

According to yet another aspect, the invention relates to use of at least one anti-CD151 antibody, or a functional fragment thereof, which is capable of inhibiting the cell adhesion of tumour cells.

As has been mentioned hereinbefore, the CD151 protein belongs to the tetraspanin family and, by virtue thereof, has 2 extracellular domains EC1 (18 amino acids, sequence [40-57]) and EC2 (109 amino acids, sequence [113-221]), also referred to as extracellular loops.

According to the present invention, the antibodies used are capable of binding to at least one epitope located in the extracellular domain. Preferably, said antibody will become fixed to the EC1 and/or EC2 loops.

More particularly, according to a preferred embodiment of the invention, there is described the use of at least one anti-CD151 antibody, or a functional fragment thereof, which is capable of binding to an epitope included in the extracellular loop 1 (EC1) and/or 2 (EC2), preferably EC2, corresponding to the amino acids 40-57 (SEQ ID No. 6) and 113-221 (SEQ ID No. 4), respectively, of the CD151 protein.

The EC1 loop [40-57] contains 18 amino acids and has a theoretical weight of 2002.2 Da.

The EC2 loop [113-221] has an N-glycosylation site (residue Asn159) and 6 cysteine residues forming 3 disulfide bridges. A structural model of the EC2 loop of the tetraspanins, and especially of CD151, has been proposed on the basis of the three-dimensional structure of the EC2 loop of the tetraspanin CD81 (Seigneuret et al., 2001, J. Biol. Chem. 276, 40055-40064). According to that model, the tetraspanins have a common, relatively conserved scaffold composed of 3α helices and a specific variable domain. For CD151, that scaffold is thought to be composed of the regions [113-157] and [209-221], and the variable domain is thought to be composed of the region [158-208].

The variable domain of the EC2 loop is thought to be more especially involved in the specific interactions of CD151 with proteins of the integrin family. Directed mutation experiments have especially shown the importance of the region [193-208], and more precisely of the tripeptide QRD [194-196] and the cysteine residue at position 192, in the association of CD151 with certain laminin receptor integrins such as integrins α3β1 or α6β4 (Kazarov et al., 2002, J. Cell Biol. 158, 1299-1309).

Still more preferably, the present invention is directed to use of at least one anti-CD151 antibody, or a functional fragment thereof, which is capable of binding to an epitope of the EC2 region comprising, at least, the amino acids Glutamine, Arginine and Aspartic Acid at positions 194, 195 and 196 (QRD$^{194-196}$), respectively, of the CD151 protein.

According to another aspect, it must be understood that the invention consists mainly of use of at least one anti-CD151 antibody, or a functional fragment thereof, which consists of a monoclonal antibody.

A "monoclonal antibody" is to be understood as an antibody derived from a population of substantially homogeneous antibodies. More especially, the individual antibodies of a population are identical with the exception of a few possible mutations that may be produced naturally and that may be present in minimal amounts. In other words, a monoclonal antibody consists of a homogeneous antibody resulting from the proliferation of just one cell clone (for example, a hybridoma, a eukaryotic host cell transfected with a DNA molecule coding for the homogeneous antibody, a prokaryotic host cell transfected with a DNA molecule coding for the homogeneous antibody etc.) and which is usually characterised by heavy chains of one and the same class and sub-class and light chains of just one type. Monoclonal antibodies are highly specific and are directed to a single antigen. In addition, in contrast to preparations of polyclonal antibodies which customarily comprise different antibodies directed to different determinants, or epitopes, each monoclonal antibody is directed to a single epitope of the antigen.

According to a particular embodiment of the invention, the monoclonal antibody used is selected from the antibodies TS151 and TS151r. In the remainder of the description, the expressions TS151r and TS151R are interchangeable.

The present invention accordingly describes use of at least one anti-CD151 antibody, or a functional fragment thereof, said antibody consisting of the TS151 antibody and/or the TS151r antibody.

More particularly, the TS151 antibody is defined in that it comprises at least:
the 3 heavy-chain CDRs CDR-H1, CDR-H2 and CDR-H3 of sequence SEQ ID No. 7, 8 and 9, respectively; and
the 3 light-chain CDRs CDR-L1, CDR-L2 and CDR-L3 of sequence SEQ ID No. 11, 12 and 13, respectively.

According to another embodiment, the antibody TS151 is characterised in that it comprises a heavy chain comprising the sequence SEQ ID No. 10 and a light chain comprising the sequence SEQ ID No. 14.

Table 1 below provides a summary of those elements.

TABLE 1

| Antibody | Light chain | Heavy chain | SEQ ID No. |
|---|---|---|---|
| TS151 | | CDR-H1 | 7 |
| | | CDR-H2 | 8 |
| | | CDR-H3 | 9 |
| | CDR-L1 | | 11 |
| | CDR-L2 | | 12 |
| | CDR-L3 | | 13 |
| | | Complete (variable domain) | 10 |
| | Complete (variable domain) | | 14 |

As for the antibody TS151r, the latter is defined in that it comprises, at least:
the 3 heavy-chain CDRs CDR-H1, CDR-H2 and CDR-H3 of sequence SEQ ID No. 15, 16 and 17, respectively; and
the 3 light-chain CDRs CDR-L1, CDR-L2 and CDR-L3 of sequence SEQ ID No. 19, 20 and 21, respectively.

According to another embodiment, the antibody TS151r is characterised in that it comprises a heavy chain comprising the sequence SEQ ID No. 18 and a light chain comprising the sequence SEQ ID No. 22.

Table 2 below provides a summary of those elements.

TABLE 2

| Antibody | Light chain | Heavy chain | SEQ ID No. |
|---|---|---|---|
| TS151r | | CDR-H1 | 15 |
| | | CDR-H2 | 16 |
| | | CDR-H3 | 17 |
| | CDR-L1 | | 19 |
| | CDR-L2 | | 20 |
| | CDR-L3 | | 21 |
| | | Complete (variable domain) | 18 |
| | Complete (variable domain) | | 22 |

According to another embodiment, Table 3 hereinbelow summarises the nucleotide sequences of the antibodies TS151 and TS151r.

TABLE 3

| Antibody | Light chain | Heavy chain | SEQ ID No. |
|---|---|---|---|
| TS151 | | CDR-H1 | 23 |
| | | CDR-H2 | 24 |
| | | CDR-H3 | 25 |
| | CDR-L1 | | 27 |
| | CDR-L2 | | 28 |
| | CDR-L3 | | 29 |
| | | Complete (variable domain) | 26 |
| | Complete (variable domain) | | 30 |
| TS151r | | CDR-H1 | 31 |
| | | CDR-H2 | 32 |
| | | CDR-H3 | 33 |
| | CDR-L1 | | 35 |
| | CDR-L2 | | 36 |
| | CDR-L3 | | 37 |
| | | Complete (variable domain) | 34 |
| | Complete (variable domain) | | 38 |

Details of the generation of said antibodies are given in Example 1. These 2 antibodies are directed to different epitopes because TS151 recognises CD151 whether it is associated with integrins or is free on the surface of the cell (Chometon et al., 2006, Exp. Cell Res. 312, 983-995), whereas TS151r does not recognise CD151-integrin complexes (Serru et al., 1999, Biochem. J. 340, 103-111; Geary et al., 2001, Tissue Antigens 58, 141-153; Kazarov et al., 2002, J. Cell Biol. 158, 1299-1309; Sterk et al., 2002, J. Cell Sci. 115, 1161-1173). The epitope recognised by TS151r is located in the EC2 loop and comprises the residues Q194, R195 and D196 (Kazarov et al., 2002, J. Cell Biol. 158, 1299-1309). This antibody is therefore directed, at least in part, at that site on CD151 which is involved in interactions with the integrins. The C192 residue may also be involved in the recognition of CD151 by TS151r (Kazarov et al., 2002, J. Cell Biol. 158, 1299-1309). The epitope of the TS151 antibody, although being different to that of TS151r, has not been precisely determined.

Treating human keratinocytes (the epithelial line HaCaT) with the TS151r antibody brings about a loss of cell-cell contact, rearrangement of the cytoskeleton, intracellular redistribution of the integrin α6β4 and an increase in the migration of cells on laminin 1 (Chometon et al., 2006, Exp. Cell Res. 312, 983-995).

More particularly, the antibody preferably used consists of the antibody TS151.

Preferably, use of the anti-CD151 antibodies in the context of cancer treatment is of value very especially in cancers overexpressing that same CD151 receptor.

Such cancers consist of colon cancer [Hashida et al., Br. J. Cancer 89 (2003):158-167], lung cancer, preferably non-small-cell lung cancer [Tokuhara et al., Clin. Cancer Res. 7 (2001):4109-4114], prostate cancer [Ang et al., Cancer Epidemiol. Biomarkers 13 (2004):17] and pancreatic cancer [Gesierich et al., Clin. Cancer Res. 11 [2005):2840-2852].

The present invention accordingly claims use of an antibody as described hereinbefore in the treatment of cancer, said cancer preferably consisting of colon, lung, prostate or pancreatic cancers.

The invention relates also to a pharmaceutical composition comprising, as active ingredient, a compound consisting of an antibody, or one of its derivative compounds or functional fragments, to which there is preferably added an excipient and/or a pharmaceutically acceptable carrier.

More especially, the invention is directed to use of an antibody according to the invention in the preparation of a pharmaceutical composition additionally comprising at least one pharmaceutically acceptable carrier.

In the present description, a pharmaceutically acceptable carrier is understood as referring to a compound or combination of compounds included in a pharmaceutical composition which does not give rise to secondary reactions and which, for example, makes it possible to facilitate the administration of the active compound(s), to increase the life and/or efficacy thereof in the body, to increase the solubility thereof in solution or to improve its storage. Such pharmaceutically acceptable carriers are well-known and will be adapted by the person skilled in the art as a function of the nature and mode of administration of the selected active compound(s).

Preferably, those compounds will be administered by a systemic route, especially the intravenous route, by the intramuscular, intradermal, intraperitoneal or subcutaneous route, or by the oral route. More preferably, the composition comprising the antibodies according to the invention will be administered on a plurality of occasions staggered over time.

Their optimal modes of administration, dosage regimens and galenic forms can be determined according to criteria generally taken into consideration in establishing a suitable treatment for a patient such as, for example, the age or bodyweight of the patient, the severity of his or her general condition, the tolerability of the treatment and the secondary effects established.

According to the invention there is described a composition for the treatment of cancer, characterised in that it comprises, as active ingredient, at least one anti-CD151 antibody, or a functional fragment thereof, which is capable of binding to the CD151 protein.

According to the invention there is described a composition for the treatment of cancer, characterised in that it comprises, as active ingredient, at least one anti-CD151 antibody, or a functional fragment thereof, which is capable of binding to the CD151 protein and/or of inhibiting its metastasis-promoting activity.

According to the invention there is also described a composition for the treatment of cancer, characterised in that it comprises, as active ingredient, at least one anti-CD151 antibody, or a functional fragment thereof, which is capable of inhibiting the development of primary tumours.

According to another aspect of the invention, there is described a composition comprising at least one anti-CD151 antibody, or a functional fragment thereof, said at least one antibody being a monoclonal antibody selected from the antibodies TS151 or TS151r.

According to yet another aspect of the invention, there is claimed a composition which comprises a combination of the antibodies TS151 and TS151r, or of functional fragments thereof.

The literature shows that the CD151 protein is overexpressed in cancers and, very especially, in colon carcinomas [Hashida et al., Br. J. Cancer 89 (2003): 158-167], non-small-cell lung cancers [Tokuhara et al., Clin. Cancer Res. 7 (2001): 4109-4114], prostate cancers [Ang et al., Cancer Epidemiol. Biomarkers 13 (2004): 1717-1721] and pancreatic cancers [Gesierich et al., Clin. Cancer Res. 11 (2005): 2840-2852].

Of course, the above list is given solely by way of illustration and any cancer must be understood as overexpressing the CD151 protein and therefore as being capable of being treated in accordance with the present invention.

Another, complementary embodiment of the invention consists of a composition as described hereinbefore which additionally comprises, as a combination product for simultaneous, separate or time-staggered use, a cytotoxic/cytostatic agent and/or a monoclonal antibody.

The present invention accordingly relates also to a composition as described hereinbefore, characterised in that it additionally comprises, as a combination product for simultaneous, separate or time-staggered use, at least one cytotoxic/cytostatic agent and/or a cell toxin and/or a radioelement and/or a monoclonal antibody.

"Simultaneous use" is understood as the administration of the two compounds of the composition according to the invention contained in one and the same pharmaceutical form.

"Separate use" is understood as the administration, at the same time, of the two compounds of the composition according to the invention contained in separate pharmaceutical forms.

"Time-staggered use" is understood as the successive administration of the two compounds of the composition according to the invention, each contained in a separate pharmaceutical form.

In general manner, the composition according to the invention considerably increases the efficacy of the cancer treatment. In other words, the therapeutic effect of the antibody according to the invention is potentiated in unexpected manner by the administration of a cytotoxic agent. Another major subsequent advantage produced by a composition according to the invention relates to the possibility of using lower effective doses of active ingredient, which makes it possible to avoid or reduce the risks of secondary effects appearing, especially the effect of the cytotoxic agent. Moreover, this composition according to the invention should make it possible to achieve the expected therapeutic effect more rapidly.

"Anti-cancer therapeutic agents" or "cytotoxic agents" should be understood as substances which, when administered to a patient, treat or prevent the development of the cancer in the patient. By way of non-limiting example of such agents there may be mentioned "alkylating" agents, antimetabolites, anti-tumour antibiotics, mitotic inhibitors, chromatin function inhibitors, anti-angiogenesis agents, anti-oestrogens, anti-androgens or immunomodulators.

Such agents are, for example, mentioned in the VIDAL, on the page devoted to compounds used in oncology and haematology in the column "Cytotoxiques" (English: cytotoxic agents); such cytotoxic compounds mentioned by way of reference to that document are mentioned here as preferred cytotoxic agents.

"Alkylating agents" refer to any substance which is capable of covalently binding to or alkylating any molecule, preferably a nucleic acid (e.g.: DNA), within a cell. As examples of such alkylating agents there may be mentioned nitrogen mustards such as mechlorethamine, chlorambucil, melphalan hydrochloride, pipobroman, prednimustine disodium phosphate or estramustine; oxazophorines such as cyclophosphamide, altretamine, trofosfamide, sulfofosfamide or ifosfamide; aziridines or ethylene-imines such as thiotepa, triethyleneamine or altetramine; nitrosoureas such as carmustine, streptozocin, fotemustine or lomustine; alkyl sulfonates such as busulfan, treosulfan or improsulfan; triazenes such as dacarbazine; and also platinum complexes such as cisplatin, oxaliplatin or carboplatin.

"Antimetabolites" refer to substances which block cell growth and/or cell metabolism by interfering with certain activities, generally DNA synthesis. By way of example of antimetabolites there may be mentioned methotrexate, 5-fluorouracil, floxuridine, 5-fluorodeoxyuridine, capecitabine, cytarabine, fludarabine, cytosine arabinoside, 6-mercaptopurine (6-MP), 6-thioguanine (6-TG), chlorodeoxyadenosine, 5-azacytidine, gemcitabine, cladribine, deoxycoformycin and pentostatin.

"Anti-tumour antibiotics" refer to compounds which can prevent or inhibit the synthesis of DNA, of RNA and/or of proteins. Examples of such anti-tumour antibiotics include doxorubicin, daunorubicin, idarubicin, valrubicin, mitoxantrone, dactinomycin, mithramycin, plicamycin, mitomycin C, bleomycin and procarbazine.

"Mitotic inhibitors" prevent the normal progression of the cell cycle and mitosis. In general, the microtubule inhibitors or "taxoids" such as paclitaxel and docetaxel are capable of inhibiting mitosis. The vinca alkaloids such as vinblastine, vincristine, vindesine and vinorelbine are also capable of inhibiting mitosis.

"Chromatin function inhibitors" or "topoisomerase inhibitors" refer to substances which inhibit the normal function of chromatin remodelling proteins such as topoisomerases I and II. Examples of such inhibitors include, for topoisomerase I, camptothecin and also its derivatives such as irinotecan or topotecan and, for topoisomerase II, etoposide, etiposide phosphate and teniposide.

"Anti-angiogenesis agents" refer to any drug, compound, substance or agent which inhibits the growth of blood vessels. Examples of anti-angiogenesis agents include, without any limitation, razoxin, marimastat, batimastat, prinomastat, tanomastat, ilomastat, CGS-27023A, halofuginone, COL-3, neovastat, BMS-275291, thalidomide, CDC 501, DMXAA, L-651582, squalamine, endostatin, SU5416, SU6668, interferon-alpha, EMD121974, interleukin-12, IM862, angiostatin and vitaxin.

"Anti-oestrogens" or "anti-oestrogen agents" refer to any substance which reduces, antagonises or inhibits the action of oestrogens. Examples of such agents are tamoxifen, toremifene, raloxifene, droloxifene, iodoxyfene, anastrozole, letrozole and exemestane.

"Anti-androgens" or "anti-androgen agents" refer to any substance which reduces, antagonises or inhibits the action of an androgen. Examples of anti-androgens are flutamide, nilutamide, bicalutamide, spironolactone, cyproterone acetate, finasteride and cimitidine.

Immunomodulators are substances which stimulate the immune system. Examples of such immunomodulators include interferons, interleukins such as aldesleukin, OCT-43, denileukin diflitox or interleukin-2, tumour necrosis factors such as tasonermin, or other types of immunomodulators such as lentinan, sizofuran, roquinimex, pidotimod, pegademase, thymopentin, poly I:C, or levamisole in combination with 5-fluorouracil.

For further details, the person skilled in the art will be able to refer to the manual published by the French Association of Teachers of Therapeutic Chemistry entitled "Traité de chimie thérapeutique, Vol. 6, Médicaments antitumoraux et perspectives dans le traitement des cancers, ed. TEC & DOC, 2003".

Preferred monoclonal antibodies are selected from isolated antibodies which are capable of specifically inhibiting the tyrosine kinase activities of the receptors IGF-IR, EGFR, HER2/neu, cMET, VEGFR, VEGF, etc. (or any other antitumour antibody known to the person skilled in the art), or functional fragments or derivative compounds thereof, and capable of inhibiting the proliferative and/or anti-apoptotic and/or angiogenic and/or metastatic dissemination-causing activities promoted by said receptors.

In an especially preferred embodiment, said composition in the form of a combination product according to the invention is characterised in that said cytotoxic agent is chemically bound to said antibody for simultaneous use.

In an especially preferred embodiment, said composition according to the invention is characterised in that said cytotoxic/cytostatic agent is selected from spindle inhibitor or stabiliser agents, preferably vinorelbine and/or vinflunine and/or vincristine.

In order to facilitate binding between said cytotoxic agent and said antibody according to the invention, it will be possible, especially, to introduce spacer molecules between the two compounds to be bound, e.g. poly(alkylene)glycols such as polyethyleneglycol, or also amino acids, or, in another embodiment, to use active derivatives of said cytotoxic agents into which there will have been introduced functions capable of reacting with said antibody according to the invention. These binding techniques are well known to the person skilled in the art and will not be elaborated upon in the present description.

According to another aspect, the invention relates to a composition characterised in that one, at least, of said antibodies, or one of their derivative compounds or functional fragments, is conjugated with a cell toxin and/or a radioelement.

Preferably, said toxin or said radioelement is capable of preventing the growth or proliferation of the tumour cell, especially of totally inactivating said tumour cell.

Preference is also given to said toxin being an enterobacterial toxin, especially *Pseudomonas* exotoxin A.

The radioelements (or radioisotopes) employed in therapy, preferably conjugated with the antibody, are radioisotopes which emit gamma rays, preferably iodine$^{131}$, yttrium$^{90}$, gold$^{199}$, palladium$^{100}$, copper$^{67}$, bismuth$^{217}$ and antimony$^{211}$. Radioisotopes which emit beta and alpha rays may also be used in therapy.

A toxin or radioelement conjugated with at least one antibody, or a functional fragment thereof, according to the invention is understood to refer to any means making it possible to bind said toxin or said radioelement to said at least one antibody, especially by covalent binding between the two compounds, with or without introduction of a linking molecule.

Among the agents allowing chemical (covalent), electrostatic or non-covalent linkage of all or some of the conjugate's elements there may be mentioned, very especially, benzoquinone, carbodiimide and, more especially, EDC (1-ethyl-3-[3-dimethylaminopropyl]-carbodiimide hydrochloride), dimaleimide, dithiobis-nitrobenzoic acid (DTNB), N-succinimidyl S-acetyl thioacetate (SATA), agents referred to as "bridging" agents having one or more groups, with one or more phenylazide groups, reacting with ultraviolet (UV) and very preferably N-[-4-(azidosalicylamino)butyl]-3'-(2'-pyridyldithio)propionamide (APDP), N-succinimidyl 3-(2-pyridyldithio)propionate (SPDP) and 6-hydrazino-nicotinamide (HYNIC).

Another form of binding, very especially for radioelements, can consist of using a bifunctional ion chelator.

Among those chelators there may be mentioned the chelators derived from EDTA (ethylenediaminetetraacetic acid) or DTPA (diethylenetriaminepentaacetic acid) that have been developed for binding metals, especially radioactive metals, and immunoglobulins. Accordingly, DTPA and its derivatives can be substituted with different groups on the carbon chain so as to increase the stability and rigidity of the ligand-metal complex (Krejcarek et al. (1977); Brechbiel et al. (1991); Gansow (1991); U.S. Pat. No. 4,831,175).

For example, DTPA (diethylenetriaminepentaacetic acid) and its derivatives, which have long been used very widely in medicine and biology either in its free form or in the form of a complex with a metal ion, has the noteworthy characteristic of forming stable chelates with metal ions and of being bound to proteins of therapeutic or diagnostic interest such as antibodies for the development of radioimmunoconjugates in cancer therapy (Meases et al., (1984); Gansow et al. (1990)).

The present invention additionally comprises use of the composition according to the invention in the preparation of a medicament.

The present invention is accordingly directed more especially to use of a composition as described hereinbefore in the preparation of a medicament intended for the treatment of cancer. Among the cancers which may be prevented and/or treated preference is given to colon, lung, prostate or pancreatic cancer.

In addition, according to an especially innovative and advantageous aspect, the present invention is directed to use of a composition as described hereinbefore in the preparation of a medicament intended for the treatment of primary tumours.

The invention relates also to the use of an antibody according to the invention in the preparation of a medicament intended for the specific targeting of a biologically active compound at cells expressing or overexpressing the CD151 receptor.

A biologically active compound is understood herein as referring to any compound capable of modifying, especially inhibiting, the activity of cells, especially their growth, their proliferation, or the transcription or translation of genes.

Other characteristics and advantages of the invention will emerge in the remainder of the description with the Examples and Figures, for which the legends are given hereinbelow.

LEGENDS FOR FIGURES

FIG. 1 shows the nucleotide sequence of the CD151 protein (SEQ ID NO:1) and protein sequence of the CD151 protein (SEQ ID NO:2), on which sequences there are shown the EC1 and EC2 loops.

Figure 4:
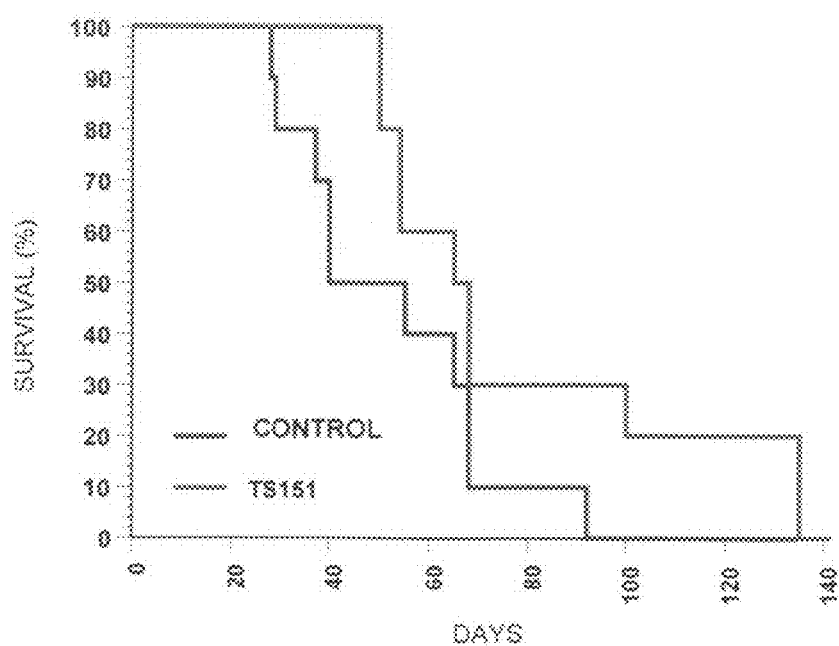

FIG. 4 shows evaluation of the in vivo anti-tumour activity of the TS151 antibody in the orthotopic model. 1×10$^6$ A549 cells are grafted into immunodepressed mice (n=10) by the intrapleural route. Seven days after grafting, the mice are treated, by the intraperitoneal route, with a challenge dose of 500 µg of TS151 antibody followed by treatment, twice a week for 5 weeks, with a dose of 250 µg of antibody per mouse. The control group is injected with PBS according to the same administration regimen.

Figure 5:
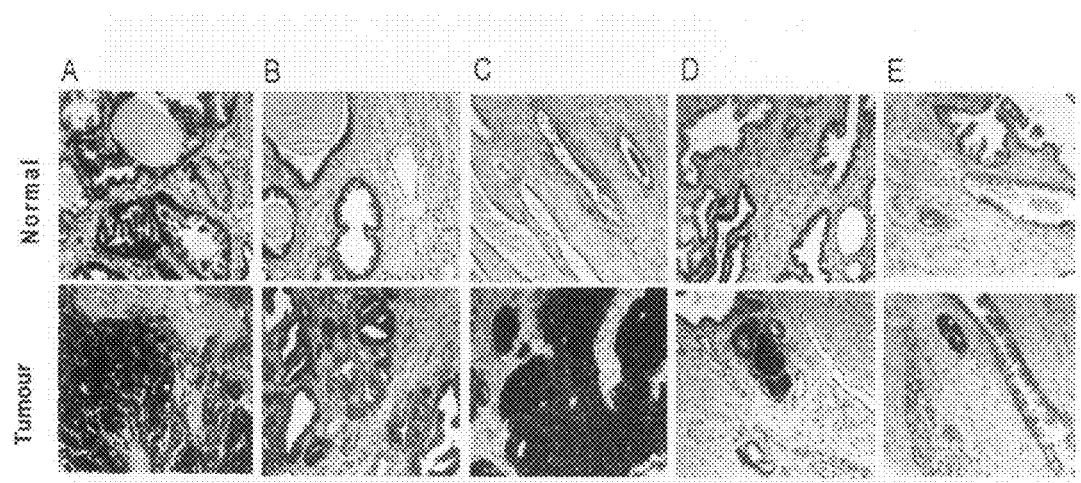

FIG. 5 illustrates expression of the CD151 molecule in patients suffering from prostate cancer. Each letter corresponds to study of one patient and for each patient the upper panel corresponds to the normal tissue adjacent to the tumour and the lower panel corresponds to the tumour tissue.

Figure 6:
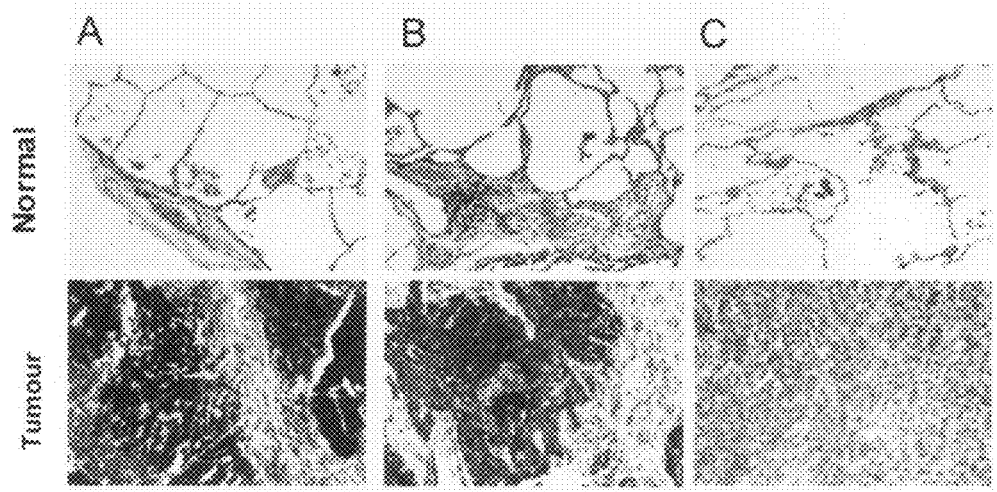

FIG. 6 illustrates expression of the CD151 molecule in patients suffering from lung cancer. Each letter corresponds to study of one patient and for each patient the upper panel corresponds to the normal tissue adjacent to the tumour and the lower panel corresponds to the tumour tissue.

Figure 7:
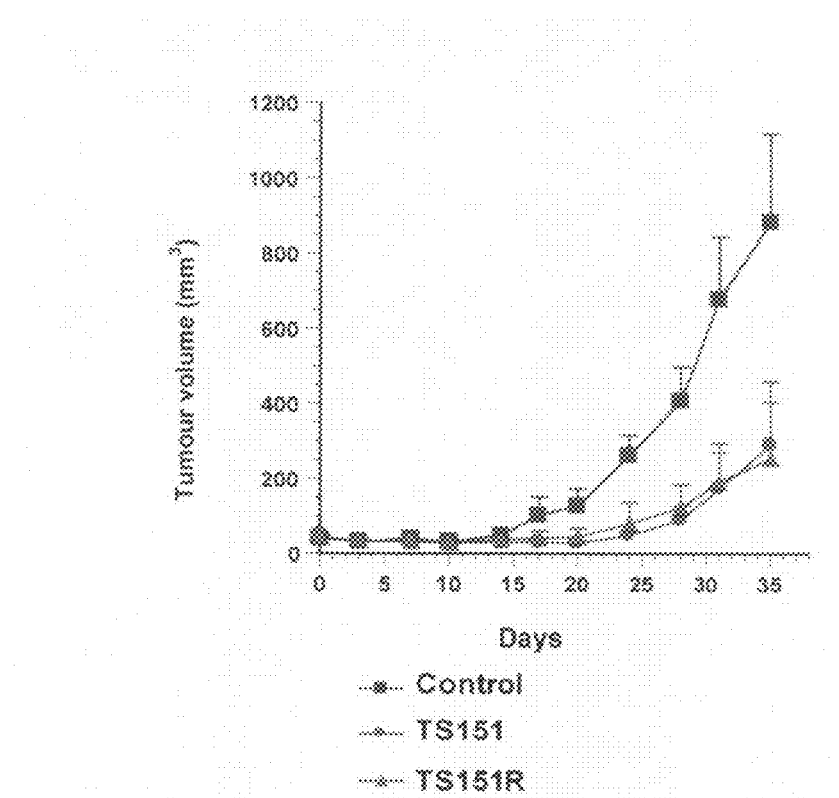

FIG. 7 illustrates the in vivo activity of the TS151 and TS151R antibodies in the PC3 xenograft model. The PC3 cells were grafted into Swiss Nude mice (n=6) by the subcutaneous route. Five days after grafting of the cells, the mice receive, by the i.p. route, a challenge dose of 2 mg/mouse of the antibodies under test followed by two administrations per week of a dose of 1 mg/mouse of those antibodies. The tumour volume is evaluated by the formula π/6×length× width×thickness, and a Mann and Whitney test is carried out for statistical evaluation of the results.

Figure 8:
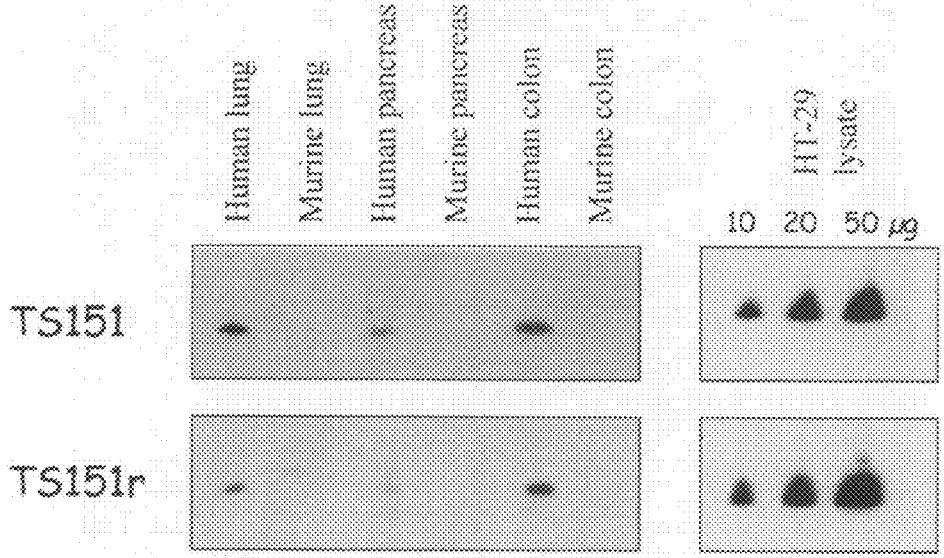

FIG. 8 illustrates evaluation of the specificity of the TS151 and TS151r antibodies for the human form of CD151 by Western blot.

FIG. 9 illustrates inhibition of the adhesion of A549 cells on laminin 5. A/ Inhibition of cell adhesion by different anti-integrin antibodies. B/ Inhibition of cell adhesion by a combination of TS151/anti-integrin α3 antibody.

EXAMPLE 1

Generation of the TS151r and TS151 Antibodies

Generation of the TS151r Antibody

In order to generate the TS151r antibody, BALB/c mice were immunised by the intraperitoneal route using $10^7$ HeLa cells. After 3 immunisations and a final booster injection, the spleen cells of a mouse were fused to P3X63AG8 myeloma cells by customary techniques described by Kohler and Milstein ($5×10^7$ spleen cells/$3×10^7$ myeloma cells). The supernatants of the hybridomas resulting from the fusion were then screened for their ability to recognise HeLa cells by means of flow cytometry and then for their ability to immunoprecipitate CD151 starting from a lysate of HeLa cells prepared in the presence of the detergent Brij 97 and to bring about the co-immunoprecipitation of CD9. The TS151r antibody was found to have those various properties.

Generation of the TS151 Antibody

In order to generate the TS151 antibody, BALB/c mice were immunised by the intraperitoneal route using $10^7$ Jurkat cells and then $10^7$ HEL cells (2 immunisations). After a final booster injection using protein complexes containing the protein ADAM10 which were obtained from lysates of Jurkat and HEL cells, the spleen cells were fused to P3X63AG8 myeloma cells by customary techniques described by Kohler and Milstein ($5×10^7$ spleen cells/$3×10^7$ myeloma cells). The supernatants of the hybridomas resulting from the fusion were firstly screened for their ability to recognise Jurkat and HEL cells by means of flow cytometry. The TS151 antibody was then selected with respect to its ability to immunoprecipitate CD151 starting from a cell lysate prepared in the presence of the detergent Brij 97 and to bring about the co-immunoprecipitation of other tetraspanins.

EXAMPLE 2

In Vivo Evaluation of the Anti-Tumour Activity of the TS151 and TS151r Antibodies in an A549 Orthotopic model Material and Method After confirmation of the expression of the CD151 protein (data not shown), the A549 cells obtained from the ATCC are routinely cultured in F12K medium, 10 mM glutamine, 10% FCS. These cells are divided 2 days before grafting so that they will be in the exponential phase of growth. For grafting, 7-week-old immunodepressed mice are anaesthetised before being administered $1×10^6$ A549 cells by the intrapleural route. The primary tumour develops rapidly and in 4 days invades the structures adjacent to the injection site including the mediastinum, the lungs and the diaphragm. In order to mimic the disease better, starting treatment is not commenced until 7 days after implanting the cells, by the intraperitoneal route. After injection of a challenge dose of 500 μg/mouse, the purified TS151 antibody is administered twice a week for 5 weeks, at a dose of 250 μg/mouse. A group of mice to which PBS is administered is introduced as a control, given that previously carried out experiments showed that administration of an IgG1 isotype control had no impact on the survival of the animals.

Figure 2:
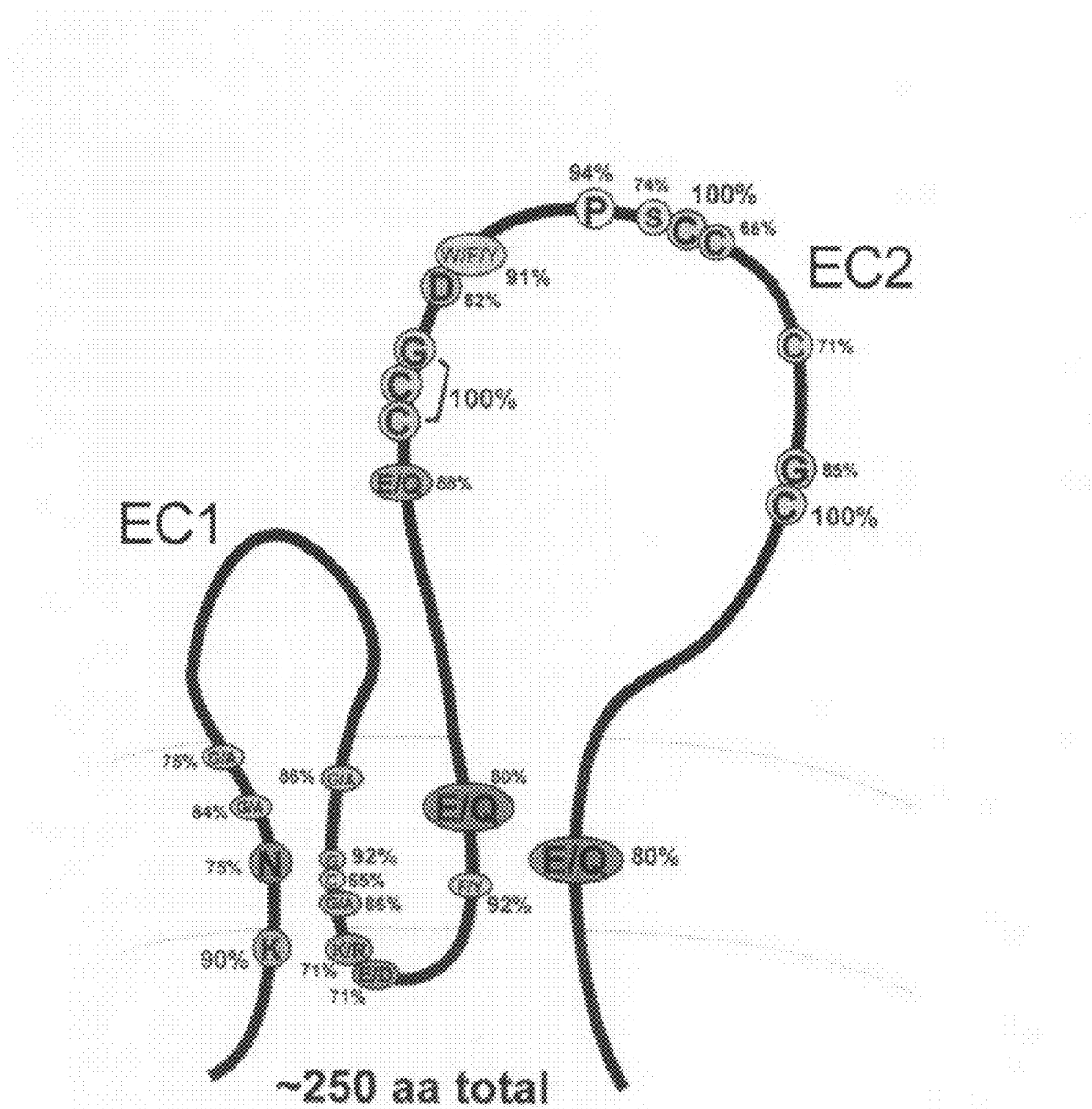
FIG. 2 is a diagram illustrating the structure of the tetraspanins, to which the CD151 protein belongs, and very especially the two extracellular loops EC1 and EC2.
Figure 3:
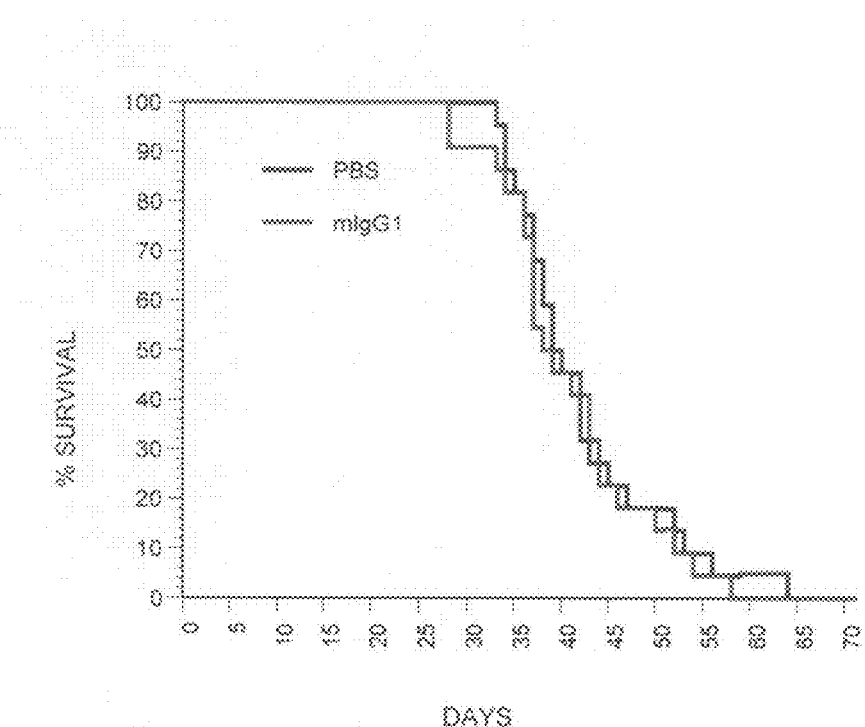
FIG. 3 shows the PBS/control antibody comparison in the A549 orthotopic model.

FIG. 3, which was obtained from preliminary data, shows the specificity of the activity observed with the anti-CD151 antibody: treatment of the animals with a murine IgG1 (mIgG1) used as isotype control shows that this has no impact on the survival of animals injected with the PBS used as carrier for those antibodies.

The evaluation parameter for this model is the survival of the animals, and the anti-tumour activity is expressed by calculation of the T/C %=median survival of the treated animals/median survival of the animals from the control group X 100. It has been established that a T/C % greater than or equal to 125% is indicative of activity of the product.

Results

FIG. 4 shows anti-tumour activity of the TS151 antibody, with a calculated T/C % of 140%.

EXAMPLE 3

Comparison of the In Vivo Anti-Tumour Activity of the TS151 and 50-6 Antibodies in an A549 Orthotopic Model Material and Method The protocol employed is the same as that of Example 2 hereinbefore.

Results

The data obtained clearly demonstrate that the TS151 antibody has anti-tumour activity which is clearly greater than that shown by the 50-6 antibody, the latter having a T/C % of only 118, that is to say less than the threshold value of 125% (data not shown).

The results obtained, namely the T/C % calculated in the manner defined hereinbefore, are shown in Table 4 below.

TABLE 4

|  | TS151 antibody | 50-6 antibody |
| --- | --- | --- |
| T/C % | 140 | 118 |

EXAMPLE 4

Study of Expression of the CD151 Molecule

The expression of the CD151 protein was researched by immunohistochemistry in samples of human tissues obtained from patients suffering from prostate cancers or lung cancer. For these patients, slides of normal tissues adjacent to the tumour were available and were therefore included in order to calibrate the level of expression in the tumour tissues versus normal tissues.

For these experiments, commercially available slides of the "Tissue array" type are used. After deparaffinisation, antigen unmasking is performed at 30° C. with the aid of an enzymatic solution containing pepsin (Labvision ref. AP-9007-005). This step is followed by a step of removal of endogenous peroxidases by incubation of the sections in a solution of hydrogen peroxide (Sigma) 0.3% in water. Saturation of the non-specific sites is then carried out with a solution of Ultra-V-Block (Labvision, ref. TA-125-UB) and labelling is carried out using a commercially available murine anti-CD151 antibody (Serotech, Ref. MCA 1856) used at a final concentration of 5 µg/ml. A murine IgG1 isotype control antibody (DakoCytomation, Ref. X0931) is used as a negative experimental control. Labelling visualisation is performed using the Envision Dual Link visualisation system (DakoCytomation, Ref. K4061) and the reference of the DAB peroxidase substrate is S3309 from DakoCytomation.

The results presented in FIG. 5 show that a number of patients developing prostate tumours exhibit overexpression of the CD151 molecule. This overexpression may be very significant for 20% of the patients studied (patients A and C) or moderate (patients A and D). It is to be noted that, except at the level of the endothelial cells, the corresponding normal prostatic tissues do not express CD151 or express it only a little and that, where it is expressed, it seems to be limited to glandular type structures. Patient E exhibits an example of a tumour not expressing CD151.

In the case of the lung cancer (FIG. 6), moderate (patient A) to marked (patient B) expression is observed in certain cells of normal pulmonary tissue. However, the tumour tissue exhibits a very high density of heavily labelled cells (patients A and B). Patient C exhibits an example of a tumour not expressing CD151.

EXAMPLE 5

Effect of the TS151 and TS151R Antibodies on In Vivo Growth of the PC3 Tumour Implanted Subcutaneously in the Nude Mouse Given the results obtained by immunohistochemistry on prostate tissue arrays, the evaluation of anti-CD151 antibodies on a PC3 tumour xenograft was planned. The PC3 line is an androgen-independent prostate line obtained from the ATCC and cultured in F12K medium+10% FCS+L-Glutamine. For evaluation, $5\times10^6$ PC3 cells are implanted in the right flank of Swiss Nude mice. Five days after implantation, the animals are randomised on the basis of tumour volume and assigned to 3 comparable groups. The tumour volume of the selected grafted animal group is between 41 and 47 mm$^3$ (volume calculated by the formula $\pi/6\times$length$\times$width$\times$thickness) on day 0 of treatment. The animals are then given the purified antibodies under test or PBS. The antibody doses and the frequency of injections is as follows: challenge dose 2 mg/dose of antibody; maintenance dose 1 mg/dose twice a week.

The results presented in FIG. 7 show that the two antibodies tested (TS151 and TS151R) behave similarly and they very significantly inhibit growth of the PC3 tumour implanted in a sub-cutaneous position in the Swiss Nude mouse. Table 5 below summarises the statistical analyses of these results.

Studies carried out in parallel and presented in FIG. 8 show that the TS151 and TS151R antibodies recognise the human CD151 molecule specifically, without any cross-reaction with the murine receptor. This observation accordingly suggests that the activity observed in the xenograft model in the Nude mouse can be attributed solely to a direct effect on the grafted human tissue and consequently excludes any possibility of the TS151 and TS151R antibodies interfering with stromal cells of the tumour or murine endothelial cells. Moreover, TS151 and TS151R are both murine IgG1 antibodies and, as a consequence and as is known to the person skilled in the art, there is little likelihood that the observed activity is due to effector functions of the ADCC and CDC type, which are more especially mediated by murine IgG2a-type antibodies in the mouse.

This set of results is therefore in agreement with a mechanism of action which is directly due to inhibition of tumour cell proliferation in vivo by the TS151 and TS151R antibodies.

EXAMPLE 6

Specificity of the TS151 and TS151r Antibodies

The specificity of the TS151 and TS151r antibodies was evaluated by Western blot. Lysates of human and murine lung, pancreas and colon tissues (Biochain, 10 µg of total proteins) and also increasing amounts of HT-29 cell lysate (10, 20 and 50 µg of total proteins) were placed on a 4-12% acrylamide gel (BioRad). After electrophoresis (non-reductive conditions), the proteins were transferred onto nitrocellulose membranes. The transfer membranes were then incubated with the purified TS151 and TS151r antibodies and then with a rabbit anti-mouse Ig polyclonal antibody coupled to peroxidase (GE Healthcare) before ECL-type visualisation.

The TS151 and TS151r antibodies exhibit specificity for the human form of CD151 as borne out by the recognition, by Western blot, of CD151 in lysates of HT-29 cells and of different tissues of human origin (FIG. 8). The absence of reactivity with murine CD151 in the lysates of various tissues sampled from the mouse confirms the specificity of the TS151 and TS151r antibodies for the human form of CD151.

EXAMPLE 7

Inhibition of Cell Adhesion

The experiments of tumour cell adhesion on laminin 5, the ligand of the integrins $\alpha3\beta1$ and $\alpha6\beta4$ with which CD151 is capable of associating, are carried out in 96-well plates. After immobilisation of laminin 5 (Chemicon, 200 µl at 1 µg/ml) for 1 hour at 37° C., the wells are saturated with BSA at 2 mg/ml (200 µl, 1 hour at 37° C.). A549 cells in suspension are

TABLE 5

|  |  | D0 | D3 | D7 | D10 | D14 |
|---|---|---|---|---|---|---|
| Control/TS151 | Mann-Whitney (Wilcoxon) | p = 0.132 | p = 0.937 | p = 0.065 | p = 0.589 | p = 0.002 |
| Control/TS151R | Mann-Whitney (Wilcoxon) | p = 0.485 | p = 0.180 | p = 0.180 | p = 0.589 | p = 0.240 |

|  | D17 | D20 | D24 | D28 | D31 | D35 |
|---|---|---|---|---|---|---|
| Control/TS151 | p = 0.002 | p = 0.002 | p = 0.002 | p = 0.002 | p = 0.002 | p = 0.002 |
| Control/TS151R | p = 0.026 | p = 0.004 | p = 0.002 | p = 0.002 | p = 0.002 | p = 0.002 | labelled using 5-chloromethylfluorescein diacetate (CM-FDA, Invitrogen) and are then added at a rate of 100000 cells (100 µl) per well in the presence or absence of antibody (100 µL). After incubation at 37° C. for 15, 30 or 60 minutes, the cells that have not adhered are removed. After reading the chemoluminescence with a luminometer (Mithras, Berthold), the percentage of adhering cells is determined with the aid of a range of CMFDA-labelled cells. The anti-CD151 antibody TS151 and the anti-integrin α3 antibody P1B5, the anti-α6 antibody NKI-Go3 and the anti-β4 antibody ASC-3 (Chemicon) are evaluated at a final concentration of 20 µg/ml. The antibody 9G4, directed to a membrane protein of *Escherichia coli*, is used as isotype control.

The anti-integrin α3 antibody P1B5 inhibits adhesion of A549 cells on laminin 5 (FIG. 9A), whereas the anti-integrin α6 antibody NKI-Go3 and the anti-integrin β4 antibody ASC-3 do not inhibit adhesion of the A549 cells on this same ligand. However, a loss of inhibition as a function of time is found, the inhibition brought about by P1B5 being greater than 90% at 15 minutes but falling to about 20% after 1 hour.

Association of the P1 B5 antibody with the anti-integrin α6 antibody NKI-Go3 or the anti-integrin β4 antibody ASC-3 allows marked inhibition of adhesion to be maintained after 1 hour, the inhibition being greater than 90% for the association with the anti-α6 antibody and being about 70% for the combination with the anti-β4 antibody. These results show that the A549 cells adhere on laminin 5 for an initial period by means of the integrin α3β1 and then for a second period by means of the integrin α6β4.

The TS151 anti-CD151 antibody does not inhibit the adhesion of the A549 cells on laminin 5 when it is used on its own (FIG. 9B). The effect of a combination of TS151 with P1B5 on adhesion of the A549 cells was then evaluated and compared with the previously mentioned combinations. This TS151/P1B5 combination gives a result which is comparable to the association of anti-α6/anti-α3 and anti-β4/anti-α3 antibodies, there being observed maintenance of inhibition of adhesion of the order of 80% after 1 hour. The TS151 antibody should therefore be capable of inhibiting the adhesion of A549 cells by way of an antagonist effect on the integrin α6β4.

The invention claimed is:

1. A method of inhibiting primary tumor growth of a CD 151-expressing human lung or human prostate cancer in a subject, comprising administering a monoclonal antibody selected from TS151 and TS151r antibodies to said subject in need thereof, wherein the TS151 antibody and/or the TS151r antibody inhibits the primary tumor growth of the human lung or the human prostate cancer.

2. The method of claim 1, wherein the TS151 antibody and the TS151r antibody are capable of inhibiting primary tumor cell proliferation of the human lung or the human prostate cancer.

3. The method of claim 1, wherein the TS151r antibody is capable of binding to an epitope in the EC2 region comprising, at least, the amino acids Glutamine, Arginine and Aspartic Acid at positions 194, 195 and 196 ($QRD^{194-196}$), respectively, of the human CD151 protein.

4. The method of claim 1, wherein the TS151 antibody comprises:
   i) three heavy chain complementarity determining regions, CDR-H1 (SEQ ID NO: 7), CDR-H2 (SEQ ID NO: 8) and CDR-H3 (SEQ ID NO: 9); and
   ii) three light chain complementarity determining regions, CDR-L1 (SEQ ID NO: 11), CDR-L2 (SEQ ID NO: 12) and CDR-L3 (SEQ ID NO: 13).

5. The method of claim 4, wherein the TS151 antibody comprises a heavy chain further comprising the sequence set forth in SEQ ID NO:10 and a light chain further comprising the sequence set forth in SEQ ID NO:14.

6. The method of claim 1, wherein the TS151r antibody comprises:
   i) three heavy chain complementarity determining regions, CDR-H1 (SEQ ID NO: 15), CDR-H2 (SEQ ID NO: 16) and CDR-H3 (SEQ ID NO: 17); and
   ii) three light chain complementarity determining regions, CDR-L1 (SEQ ID NO: 19), CDR-L2 (SEQ ID NO: 20) and CDR-L3 (SEQ ID NO: 21).

7. The method of claim 6, wherein the antibody comprises a heavy chain further comprising the sequence set forth in SEQ ID NO:18 and a light chain further comprising the sequence set forth in SEQ ID NO:22.

8. The method of claim 1, wherein the TS151 antibody and/or the TS151r antibody is in the form of a pharmaceutical composition additionally comprising at least one pharmaceutically acceptable carrier.

9. A composition for the treatment of human lung or human prostate cancer cells which overexpress a human CD151 protein, comprising as an active ingredient, a TS151 antibody and/or a TS151r antibody, wherein administering the TS151 antibody and/or the TS151 r antibody inhibits primary tumor growth of the human lung or the human prostate cancer.

10. The composition of claim 9, which is comprised in a combination product, which combination product additionally comprises at least one other agent selected from a cytotoxic/cytostatic agent, cell toxin, radioelement and monoclonal antibody.

11. The composition of claim 10, wherein a TS151 antibody and/or a TS151r and the at least one other agent are administered to a human or animal subject in a simultaneous, separate or time-staggered regimen.

* * * * *